United States Patent
Bruun et al.

(10) Patent No.: US 11,633,351 B2
(45) Date of Patent: Apr. 25, 2023

(54) FAST DISINTEGRATING CANNABINOID TABLETS

(71) Applicant: NordicCan A/S, Vejle (DK)

(72) Inventors: Heidi Ziegler Bruun, Vejle Ost (DK); Dorthe Schackinger Boesen, Vejle (DK); Bruno Provstgaard Nielsen, Vejle Øst (DK)

(73) Assignee: NordicCan A/S

( * ) Notice: Subject to any disclaimer, the term of this patent is extended or adjusted under 35 U.S.C. 154(b) by 256 days.

(21) Appl. No.: 16/713,580

(22) Filed: Dec. 13, 2019

(65) Prior Publication Data

US 2021/0177748 A1 Jun. 17, 2021

(51) Int. Cl.
*A61K 9/28* (2006.01)
*A61K 9/00* (2006.01)
*A61K 9/20* (2006.01)
*A61K 31/05* (2006.01)

(52) U.S. Cl.
CPC .......... *A61K 9/0056* (2013.01); *A61K 9/2018* (2013.01); *A61K 9/2027* (2013.01); *A61K 9/2054* (2013.01); *A61K 9/2059* (2013.01); *A61K 9/2886* (2013.01); *A61K 31/05* (2013.01)

(58) Field of Classification Search
CPC ...... A61K 9/0056; A61K 9/0058; A61K 9/20; A61K 31/352; A61K 9/2054; A61K 9/2018; A61K 9/2059
See application file for complete search history.

(56) References Cited

U.S. PATENT DOCUMENTS

| | | | |
|---|---|---|---|
| 6,730,330 B2 | 5/2004 | Whittle et al. | |
| 8,735,374 B2 | 5/2014 | Zerbe et al. | |
| 10,406,105 B2 * | 9/2019 | Kolter | A61P 25/18 |
| 10,772,837 B2 * | 9/2020 | Lefler | A61K 31/135 |
| 10,925,853 B2 * | 2/2021 | Bruun | A61K 31/192 |
| 2010/0034888 A1 | 2/2010 | Pellikaan et al. | |
| 2016/0015683 A1 * | 1/2016 | McCarty | A61K 9/2018 206/528 |
| 2016/0220593 A1 | 8/2016 | Anastassov et al. | |
| 2017/0157041 A1 | 6/2017 | Goldner | |
| 2017/0368020 A1 | 12/2017 | Estey et al. | |
| 2018/0042842 A1 | 2/2018 | Whittle et al. | |
| 2018/0071350 A1 | 3/2018 | Kolsky | |
| 2018/0221304 A1 | 8/2018 | Small-Howard et al. | |
| 2018/0221332 A1 | 8/2018 | Renwick et al. | |
| 2018/0263913 A1 | 9/2018 | Lefler et al. | |

FOREIGN PATENT DOCUMENTS

| | | |
|---|---|---|
| CA | 1664311 C | 3/2008 |
| EP | 2061427 B1 | 7/2011 |
| EP | 2609912 A1 | 7/2013 |
| WO | 2015131269 A1 | 9/2015 |
| WO | 2016126592 A1 | 8/2016 |
| WO | 2017183011 A1 | 10/2017 |
| WO | 2017223309 A1 | 12/2017 |
| WO | 2018022669 A1 | 2/2018 |
| WO | 2018089863 A1 | 5/2018 |
| WO | 2018141050 A1 | 8/2018 |
| WO | 2018142403 A1 | 8/2018 |
| WO | 2018144637 A1 | 8/2018 |
| WO | 2019126872 A1 | 7/2019 |
| WO | 2019204708 A1 | 10/2019 |
| WO | WO-2020211913 A1 * | 10/2020 ............. A61K 31/05 |

OTHER PUBLICATIONS

International Search Report and Written Opinion for application No. PCT/DK2020/050102 dated Jul. 16, 2020.

* cited by examiner

*Primary Examiner* — Lakshmi S Channavajjala
(74) *Attorney, Agent, or Firm* — St. Onge Steward Johnston & Reens LLC

(57) ABSTRACT

The present invention relates in a first aspect to a fast disintegrating cannabinoid tablet, the tablet comprising a sugar alcohol composition comprising one or more sugar alcohol particles in an amount of at least 20% by weight of the tablet, a cannabinoid composition comprising one or more cannabinoids, and a disintegrant composition comprising one or more disintegrants operable to disintegrate the tablet within a period of 2 minutes or less in contact with oral saliva. In a second aspect, the invention relates to a modular tablet, wherein the tablet comprises a further tablet module that is different in composition.

21 Claims, No Drawings

FAST DISINTEGRATING CANNABINOID TABLETS

FIELD OF THE INVENTION

The invention relates to the field of oral delivery vehicles for alleviation or treatment of a condition with one or more cannabinoids. In particular, the invention relates to fast disintegrating tablets for oral administration of one or more cannabinoids.

BACKGROUND OF THE INVENTION

Cannabinoids are a group of chemicals found in *Cannabis sativa, Cannabis indica, Cannabis ruderalis,* Marijuana plant and related plant species. They are known to activate cannabinoid receptors (CB1 and CB2). These chemicals are also produced endogenously in humans and other animals. Cannabinoids are cyclic molecules exhibiting particular properties such as being lipophilic, have the ability to easily cross the blood-brain barrier, and having low toxicity.

*Cannabis sativa* contains more than 400 chemicals and approximately 120 cannabinoids, the active constituents of *Cannabis*, including tetrahydrocannabinol (THC), cannabidiol (CBD), cannabinol (CBN), tetrahydrocannabivarin (THCV) and cannabigerol (CBG). Pharmacologically, the principal psychoactive constituent of *Cannabis* is tetrahydrocannabinol (THC), which is used for treating a wide range of medical conditions, including glaucoma, AIDS wasting, neuropathic pain, treatment of spasticity associated with multiple sclerosis, fibromyalgia and chemotherapy-induced nausea. THC is also effective in the treatment of allergies, inflammation, infection, depression, migraine, bipolar disorders, anxiety disorder, drug dependency and drug withdrawal syndromes.

Cannabinoid delivery methods have been the attention of more and more interest in recent years. Lung delivery is most commonly achieved by smoking *Cannabis*. However, there are health concerns for this mode of administration. *Cannabis* smoke carries even more tars and other particulate matter than tobacco. Furthermore, many patients find the act of smoking unappealing, as well as being generally unhealthy.

Attempts have been made to overcome some of the problems associated with smoking both *Cannabis* and tobacco by providing various smokeless inhalable aerosol formulations for lung delivery. These formulations were found to be of varying effectiveness in delivering the active agent to the lungs and compliance was an issue even with proper training on the use of inhalation devices.

In formulating tablets, various challenges are associated with obtaining a homogenous mixture where variations are avoided and a safe and convenient delivery may be obtained. Also, the general formulation of the tablets offering convenience to the user need not be compromised which is often the case if conventional delivery means are applied.

One of the challenges with tablets as a delivery vehicle of cannabinoids is that cannabinoids tend to be associated with off notes during administration due to the specific physio-chemical properties of the compounds. The taste masking challenge is more profound when a higher release of cannabinoids are intended in tablets for oral administration. If off-notes are the predominant sensation during administration, convenience may be affected and even more critically, the delivery of cannabinoids may also be affected. Saliva production may be suppressed, and the delivery vehicle may not be handled correctly.

Furthermore, it is important that a formulation is provided that may also help in obtaining a release profile of cannabinoids that offers increased convenience and effectiveness. In general, less attention is given in the prior art on the impact of the tablet formulation for the sensorics properties of oral cannabinoid delivery. Here, important sensorics properties include friability, hardness, texture, flavor perception, sweetness perception and off-notes associated with cannabinoids. These properties are both relevant from a convenience perspective in tablets for oral administration, but certainly also in order to support an appropriate delivery of cannabinoids from tablets and avoid adverse side effects of cannabinoids.

Hence, there is a need in the prior art for improved tablet formulations that solve the above-referenced challenges and problems of the prior art. In particular, there is a need in the prior art for new tablets that support appropriate fast delivery of cannabinoids combined with beneficial sensorics properties.

SUMMARY OF THE INVENTION

Accordingly, in one aspect of the invention there is provided a fast disintegrating cannabinoid tablet, the tablet comprising a sugar alcohol composition comprising one or more sugar alcohol particles in an amount of at least 20% by weight of the tablet, a cannabinoid composition comprising one or more cannabinoids, and a disintegrant composition comprising one or more disintegrants operable to disintegrate the tablet within a period of 2 minutes or less in contact with oral saliva.

Providing a fast disintegrating cannabinoid tablet according to the invention may solve various problems of the prior art and aims at establishing a formulation that combines beneficial delivery properties of cannabinoids combined with advantageous sensorics properties.

Generally, the tablet according to the invention disintegrates within a relatively short period of time without contributing significantly to off notes from the cannabinoids released during use of the tablet. The tablet is intended to disintegrate in the mouth without masticating, mainly with supply of saliva already present in the oral cavity or saliva generation during use of the tablet. Hence, the tablet is neither to be chewed nor to be swallowed but is to be kept in place in the mouth or swished forth and back in the mouth in the same way as a cleansing system for the oral cavity.

One of the attributes of the invention is the surprising recognition that it is possible to provide a tablet with fast disintegrating properties and at the same time secure beneficial sensorial properties, including insignificant or less profound off note taste from the cannabinoids employed. The inventors of the applications did not expect that a fast release of cannabinoids would be possible without compromising the sensorial parameters of the tablet. The special properties of cannabinoids, such as CBD, was not considered to allow for such fast disintegration and release of the active ingredient. It is considered that cannabinoids as a diverse group of active ingredients generally are subject to a prejudice within the art in terms of taste properties in oral tablet formulations. Also, the properties of cannabinoids as a diverse group of active ingredients, such as lipophilic properties, would not have been expected to work properly in such fast disintegrating tablets. In particular this includes CBD and CBDA. More particularly this includes extracts of cannabinoids, such as extracts of CBD and CBDA. Thus, in the art of cannabinoids a person of ordinary skill in the art would not expect that fast disintegrating tablets according to the invention would be feasible.

Specifically, the content of disintegrants greatly facilitate disintegration of the tablet according to the invention. However, while disintegrants have previously been used in tablet formulation science, the particular combination of disintegrants with cannabinoids according to the application would have been seen as problematic in view of the specific properties of cannabinoids, such as CBD. Various problems were suspected by the inventors of the present application, such as sensorial drawbacks and concentration issues with a high load of the active ingredients.

With respect to release properties, the present invention may offer an improved release profile of cannabinoids compared to conventional lozenge formulations. In particular, the specific tablet of the present invention may serve to provide improved release characteristics of cannabinoids compared to conventional lozenge formulation platforms applied in combination with cannabinoids. The improved release combined with the lipophilic characteristics of cannabinoids, such as CBD, would have been expected to be contravening. However, the inventors recognized that delivery of cannabinoids were surprisingly beneficial.

In addition, the present invention may serve to provide fast and controlled release of cannabinoids such that the tablet formulation is tailored to deliver an effective content of cannabinoids over time and at the same time avoid adverse effects of cannabinoids, such as off-notes.

A very important aspect of the present invention is the provision of beneficial sensorics properties. Here, important sensorics properties include friability, texture, flavor perception, sweetness perception and off-notes associated with cannabinoids. These properties are both relevant from a convenience perspective in tablets, but certainly also in order to support an appropriate delivery of cannabinoids from a formulation, such as an improved release profile, and avoid adverse side effects of cannabinoids.

The present inventors have shown very surprising results with the specific combination of features of the present invention in terms of these sensorics properties. It was an unexpected result that the invention could both contribute to an improved release profile, such as rapid release of cannabinoids, and at the same time provide very beneficial sensorics properties which in terms may also support an appropriate delivery of cannabinoids from tablets with oral uptake and avoid adverse side effects of cannabinoids.

One of the sensorics properties that are particularly advantageous is friability of the tablet. Both in order to secure a desired release of cannabinoids and to improve the sensation by a consumer, it is critical that friability is balanced. Also, the texture of the tablet formulation during use is critical for the release of cannabinoids and the experience as well as convenience during use. These properties may be improved by the present invention which was not expected by the inventors of the present invention.

Advantageously, the compositions of the present invention can be formulated in much smaller tablets than traditional cannabinoid containing lozenges and, thus, may have reduced dissolution times in the oral cavity while still achieving significant cannabinoid plasma level and obtaining comparable cannabinoid pharmacokinetic profiles to the traditional lozenge. By reducing dissolution time and improving the speed of cannabinoid absorption, patient compliance may also be improved.

In an embodiment of the invention, the one or more disintegrants is operable to disintegrate the tablet within a period of 1.5 minutes or less in contact with oral saliva.

In an embodiment of the invention, the one or more disintegrants is operable to disintegrate the tablet within a period of 1 minute or less in contact with oral saliva.

In an embodiment of the invention, the one or more disintegrants is operable to disintegrate the tablet within a period of 0.5 minute or less in contact with oral saliva.

In the present context, "operable" or "operable to disintegrate" is intended to mean that the tablet upon administration is able to disintegrate passively by means of saliva interaction and would not need to be masticated or otherwise forced to disintegrate. In other embodiments, the tablet disintegrates within a period of 1.5 minutes or less in contact with oral saliva. In other embodiments, the tablet disintegrates within a period of 1 minutes or less in contact with oral saliva. In other embodiments, the tablet disintegrates within a period of 0.5 minute or less in contact with oral saliva.

In the present context, "disintegrated" or "disintegrate" is intended to mean that the tablet is no longer to be considered a tablet but the tablet has been reduced and/or dispersed in saliva.

In the present context, the tablet is intended to mean a "fast disintegrating tablet" ("FDT"), or similar wording, such as "orally disintegrating tablet" ("ODT"). If not stated otherwise, if the tablet according to the invention is made as one module, contrary to two or more modules, then the tablet is intended to be an FDT tablet. If on the other hand, the tablet is made of more than one module, such as two modules, such additional module is intended to be a "lozenge" module, which provides a longer disintegration time compared to the FDT module according to the invention. The combination of a "FDT" module and a "lozenge" module is addressed later in this application and contributes to another aspect of the invention. A "lozenge" module according to the invention may also comprise elements from the "FDT" modules but is generally different in composition, providing an extended disintegration time.

Importantly, the improved sensorics characteristics of the tablet formulation of the invention also accommodates an improved release rate of cannabinoids. The reason may be attributed to the fact that if the initial impression by the user is improved and the tablet texture is also improved, this would trigger the user to effectively use the product. Also, the production of saliva may be enhanced once the product formulation is improved, which in turn may accommodate further increased release of cannabinoids. However, the precise mechanism is not well understood.

Formulation of tablets according to the invention was seen to provide a beneficial disintegration compared to traditional tablet formulations known in the art. Surprisingly, it was seen that a disintegration time of less than 30 seconds were possible without compromising the properties of the tablet according to the invention. Sensorial properties were only insignificantly or only to a less degree affected by such a short period of disintegration time. Followingly, the fast disintegrating tablets according to the invention may provide potential relatively quick alleviation or treatment response time.

In some embodiments of the invention, the composition in contact with saliva has a disintegration profile that varies less than 10% under a compression pressure of 10 to 30 kN. In the present context "disintegration profile" is intended to mean that the weight percent total loss of material from the tablet for a given time during use varies less than 10% under a tableting force from 10 to 30 kN. The measurement is generally measured while the tablet is not completely "disintegrated". The measurement is taken while the tablet is in contact with saliva as an in vivo measurement according to the measurement outlined in the examples of the invention.

In an embodiment of the invention, the one or more disintegrants is present in an amount of 0.5 to 25% by weight of the tablet.

In some embodiments of the invention, the one or more disintegrants is present in an amount of 0.5 to 20% by weight of the tablet. In some embodiments of the invention, the one or more disintegrants is present in an amount of 0.5 to 15% by weight of the tablet. In some embodiments of the invention, the one or more disintegrants is present in an amount of 1 to 25% by weight of the tablet. In some embodiments of the invention, the one or more disintegrants is present in an amount of 1 to 20% by weight of the tablet.

In an embodiment of the invention, the one or more disintegrants is present in an amount of 2 to 15% by weight of the tablet.

In some embodiments of the invention, the one or more disintegrants is present in an amount of 2 to 10% by weight of the tablet. In some embodiments of the invention, the one or more disintegrants is present in an amount of 3 to 15% by weight of the tablet. In some embodiments of the invention, the one or more disintegrants is present in an amount of 4 to 15% by weight of the tablet. In some embodiments of the invention, the one or more disintegrants is present in an amount of 5 to 15% by weight of the tablet.

In an embodiment of the invention, the one or more disintegrants is swellable in contact with oral saliva. This implies that the tablet upon saliva contact is broken into smaller pieces.

In an embodiment of the invention, the one or more disintegrants comprises starch. This may in particular be the case when ready to use disintegrant systems are employed, such as Pearlitol Flash that contains and amount of starch.

In an embodiment of the invention, the one or more disintegrants comprises microcrystalline cellulose.

In an embodiment of the invention, the one or more disintegrants comprises low-substituted hydroxypropyl cellulose (LHPC).

In an embodiment of the invention, the one or more disintegrants comprises a super disintegrant. By "super disintegrant" the intended meaning is a disintegrant that provide a disintegrant effect that is superior compared to more traditional disintegrant used in tablet manufacture.

In an embodiment of the invention, the one or more disintegrants comprises a super disintegrant in an amount of 2 to 15% by weight of the tablet.

In some embodiments of the invention, the one or more super disintegrants is present in an amount of 2 to 10% by weight of the tablet. In some embodiments of the invention, the one or more super disintegrants is present in an amount of 3 to 15% by weight of the tablet. In some embodiments of the invention, the one or more super disintegrants is present in an amount of 4 to 15% by weight of the tablet. In some embodiments of the invention, the one or more super disintegrants is present in an amount of 5 to 15% by weight of the tablet.

In an embodiment of the invention, the one or more disintegrants comprises a super disintegrant of a cross-linked polymer.

In an embodiment of the invention, the one or more disintegrants comprises a super disintegrant selected from the group consisting of sodium croscarmellose, crospovidone, sodium starch glycolate and combinations thereof.

In an embodiment of the invention, the one or more disintegrants comprises cross-linked polyvinylpyrrolidone.

In an embodiment of the invention, the one or more disintegrants comprises cross-linked polyvinylpyrrolidone and wherein at least 50% by weight of the cross-linked polyvinylpyrrolidone has a particle size below 50 micrometers.

In an embodiment of the invention, the one or more disintegrants comprises cross-linked polyvinylpyrrolidone and wherein at least 25% by weight of the cross-linked polyvinylpyrrolidone has a particle size below 15 micrometers.

In an embodiment of the invention, the one or more solid particles are water insoluble.

In an embodiment of the invention, the plurality of solid particles are selected from the group consisting of silica, microcrystalline cellulose, cellulose, silicified microcrystalline cellulose, clay, talc, starch, pregelatinized starch, calcium carbonate, dicalcium phosphate, magnesium carbonate, magnesium-alumino-metasilicates, hyper porous silica and mixtures thereof. In some embodiments of the invention, silica is less preferred in the master granule component. In some embodiments of the invention, silica is to be avoided in the master granule component.

In an embodiment of the invention, the plurality of solid particles comprise microcrystalline cellulose.

In an embodiment of the invention, the one or more solid particles are water-soluble.

In an embodiment of the invention, the plurality of solid particles comprise one or more sugar alcohols. In an embodiment of the invention, the solid particles comprise directly compressible (DC) sugar alcohols. In an embodiment of the invention, the solid particles comprise non-directly compressible (non-DC) sugar alcohols.

In an embodiment of the invention, the one or more solid particles are selected from the group consisting of xylitol, lactitol, sorbitol, maltitol, erythritol, isomalt and mannitol, and mixtures and combinations thereof.

In an embodiment of the invention, the one or more sugar alcohol particles is present in an amount of at least 30% by weight of the tablet. In an embodiment of the invention, the one or more sugar alcohol particles is present in an amount of at least 40% by weight of the tablet. In an embodiment of the invention, the one or more sugar alcohol particles is present in an amount of at least 50% by weight of the tablet. In an embodiment of the invention, the one or more sugar alcohol particles is present in an amount of at least 60% by weight of the tablet.

In an embodiment of the invention, the one or more sugar alcohol particles is selected from the group consisting of xylitol, lactitol, sorbitol, maltitol, erythritol, isomalt and mannitol, and mixtures and combinations thereof. In an embodiment of the invention, the one or more sugar alcohols are in free form.

In some embodiments of the invention, the content of sugar alcohol in the composition is more than 70% by weight of the composition, such as more than 80% by weight of the composition.

In an embodiment of the invention, at least a part of the one or more cannabinoids is reversibly associated with at least a part of the one or more solid materials, such as microcrystalline cellulose.

The solid component may serve to obtain a more homogeneous mixture of cannabinoids in addition to the aforementioned benefits. However, due to the nature of the materials, such as friability properties, it may in some embodiments be an advantage that the materials are only present in an amount less than the amount of free sugar alcohol particles. On the other hand, it may be an advantage to have a certain amount of the materials combined with cannabinoids to secure a homogeneous mixture of the tablets.

In an embodiment of the invention, at least a part of the one or more cannabinoids is reversibly associated with at least a part of the one or more sugar alcohol particles.

In an embodiment of the invention, at least a part of the one or more cannabinoids is reversibly associated with 1:10 to 1:4 by weight of the one or more sugar alcohol particles. In an embodiment of the invention, at least a part of the one or more cannabinoids is reversibly associated with 1:30 to 1:2 by weight of the one or more sugar alcohol particles. In an embodiment of the invention, at least a part of the one or more cannabinoids is reversibly associated with 1:20 to 1:3 by weight of the one or more sugar alcohol particles.

In some embodiments of the invention, at least a part of the one or more cannabinoids is reversibly associated with 1:15 to 1:3 by weight of the one or more sugar alcohol particles. In some embodiments of the invention, at least a part of the one or more cannabinoids is reversibly associated with 1:20 to 1:2 by weight of the one or more sugar alcohol particles.

In the present context the wording "cannabinoids reversibly associated with the one or more solid particles" or "cannabinoids reversibly associated with the one or more sugar alcohol particles" or similar wording is intended to mean that the one or more cannabinoids are in contact with the one or more solid particles and are not loosely distributed within the material. During storage of the tablet composition and during storage of a tablet, the one or more cannabinoids are generally associated with the one or more solid particles. This may be in form of physical attachment, encapsulation, incorporation, solution, chemical interactions, or the like. However, during use in the oral cavity in contact with saliva, the intention is that the cannabinoids may be detached or released from the one or more solid particles, so that the one or more cannabinoids may target mucosal surfaces. The meaning of "reversibly" is therefore intended to mean that the one or more solid particles work as a means to carry the one or more cannabinoids before use and to secure delivery of the one or more cannabinoids. Also, the one or more solid particles may work to secure a microenvironment that may provide a more stable composition. Furthermore, the one or more solid particles may secure that the one or more cannabinoids are targeted to their site of action, i.e. the mucosal membrane.

In an embodiment of the invention at least a part of the one or more cannabinoids is reversibly associated with at least a part of the one or more sugar alcohol particles by means of agglomeration. In an embodiment of the invention, the agglomeration is obtained through wet granulation. In an embodiment of the invention, the agglomeration is obtained through dry granulation.

In an embodiment of the invention, at least a part of the one or more cannabinoids is reversibly associated with at least a part of the one or more sugar alcohol particles by means of a plurality of granules with a volume weighted mean diameter of 10-400 μm.

Granules are preferred in some embodiments. A common problem associated with transmucosal administration via the buccal route is swallowing due to the continuous secretion of saliva in the oral cavity. For optimal drug delivery, the tablet formulation may preferably remain in contact with oral mucosa for a time sufficient to allow for the absorption of the one or more cannabinoids. More specifically, tablet formulations may preferably not be washed away by saliva into the gastrointestinal tract if buccal absorption is the target. However, the rate of disintegration or dissolution of the tablet formulation may preferably not be so slow as to cause discomfort or inconvenience for the user. Additionally, suitable tablet formulations may preferably be small in size and designed so that the shape avoids discomfort to the patient during use. Most importantly the formulation may preferably be designed so that the cannabinoid is in a solution which optimizes its transmucosal permeation. These considerations may be obtained with a pre-mixture of the present invention.

In an embodiment of the invention, at least a part of the one or more cannabinoids is reversibly associated with at least a part of the one or more sugar alcohol particles by means of a plurality of granules with a volume weighted mean diameter of 50-300 μm.

In an embodiment of the invention, at least a part of the one or more cannabinoids is reversibly associated with at least a part of the one or more solid particles by means of a premixture.

In an embodiment of the invention, at least a part of the one or more cannabinoids is reversibly associated with at least a part of the one or more sugar alcohol particles by means of a premixture.

In the present context, a "premixture" or similar wording is intended to mean that the one or more cannabinoids have been mixed with the one or more solid particles, such as solid sugar alcohol particles, prior to being applied in the tablet formulation together with the sugar alcohol formulation.

In the present context, a premixture is partly used to allocate the one or more cannabinoids properly to the manufacturing process and secure that the uniformity is not compromised and that the cannabinoids are distributed properly into the mixture. Preferably, the cannabinoids are provided in a premixture with one or more sugar alcohols. It was a surprise to the inventors that a premixture was important to have in order for the cannabinoids to be distributed properly in the manufacturing process and to end up with a product where the uniformity was consistent.

In an embodiment of the invention, at least a part of the one or more cannabinoids is reversibly associated with at least a part of the one or more sugar alcohol particles by means of adsorption in a premixture.

In an embodiment of the invention, at least a part of the one or more cannabinoids is reversibly associated with at least a part of the one or more sugar alcohol particles by means of adsorption and wherein the one or more cannabinoids is applied by spraying.

In an embodiment of the invention, the particles comprise one or more cannabinoid solvents into which the one or more cannabinoids are solvated, such as glycol, alcohol or alkyl solvents or mixtures thereof. This may for instance be the case where an isolated cannabinoid is applied, such as a solid isolated cannabinoid.

In an embodiment of the invention, the one or more cannabinoid solvents are selected from the group consisting of polyethylene glycol, ethanol, substituted polyethylene glycols, diethylene glycol monoethyl ether, propylene glycol, propylene carbonate, or a mixture thereof.

In an embodiment of the invention, the tablet is compressed at a pressure of more than 10 kN. In an embodiment of the invention, the tablet is compressed at a pressure of more than 15 kN. In an embodiment of the invention, the tablet is compressed at a pressure of less than 30 kN.

In an embodiment of the invention, at least a part of the one or more cannabinoids is reversibly associated with at least a part of the one or more sugar alcohol particles, reducing compressibility of the composition compared to a composition where the one or more cannabinoids is not reversibly associated with at least a part of the one or more sugar alcohol particles.

In an embodiment of the invention, the tablet in contact with saliva has a disintegration profile that varies less than 10% under a compression pressure of 10 to 30 kN.

In an embodiment of the invention, the tablet in contact with saliva has a disintegration profile that varies less than 5% under a compression pressure of 10 to 30 kN.

In some embodiments of the invention, the composition in contact with saliva has a disintegration profile that is substantially the same under a compression pressure of 10 to 30 kN.

One of the observations with great impact of the present invention is that the compression force generally does not have a high influence on the disintegration time of the tablets and even not on the dissolution time of the tablets. Common understanding in the art of tableting is that the compression force has a huge influence on the disintegration time and dissolution time of tablets. The inventors have discovered that the present formulation of cannabinoids is very advantageous in this aspect.

In an embodiment of the invention, the weight ratio of the one or more cannabinoids relative to the one or more sugar alcohol particles is from 1:30 to 1:1. In an embodiment of the invention, the weight ratio of the one or more cannabinoids relative to the one or more sugar alcohol particles is from 1:20 to 1:10.

In an embodiment of the invention, the tablet is further comprising a binder, such as a dry or wet binder.

In an embodiment of the invention, the tablet is further comprising at least one dissolution modifier selected from the group consisting of acacia, agar, alginic acid or a salt thereof, carbomer, carboxymethylcellulose, carrageenan, cellulose, chitosan, copovidone, cyclodextrins, ethylcellulose, gelatin, guar gum, hydroxyethyl cellulose, hydroxyethyl methylcellulose, hydroxypropyl cellulose, hypromellose, inulin, methylcellulose, pectin, polycarbophil or a salt thereof, polyethylene glycol, polyethylene oxide, polyvinyl alcohol, pullulan, starch, tragacanthin, trehalose, xanthan gum and mixtures thereof.

In an embodiment of the invention, the tablet is further comprising at least one dissolution modifier selected from the group consisting of alginic acid or a salt thereof, polycarbophil or a salt thereof, xanthan gum and mixtures thereof.

In an embodiment of the invention, the tablet is further comprising at least one dissolution modifier selected from the group consisting of sodium alginate, calcium polycarbophil, xanthan gum and mixtures thereof.

In an embodiment of the invention, the tablet is further comprising at least one viscolising agent that when hydrated forms a gel having positive surface electrical charge and at least one viscolising agent that when hydrated forms a gel having negative surface electrical charge.

In an embodiment of the invention, the tablet is further comprising at least one alkaline buffering agent selected from the group consisting of sodium carbonate, sodium bicarbonate, potassium phosphate, potassium carbonate and potassium bicarbonate, and mixtures thereof.

In an embodiment of the invention, the tablet is further comprising at least one excipient selected from the group consisting of high intensity sweeteners, flavors, chelating agents, glidants or colorants.

In an embodiment of the invention, the unit weight of the tablet is from about 50 mg to about 250 mg. In an embodiment of the invention, the unit weight of the tablet is from about 75 mg to about 150 mg. This is particularly the case when a tablet of only one module is made, such as when the tablet is a fast disintegrating tablet without any lozenge modules.

In an embodiment of the invention, the average particle size of the sugar alcohol composition is less than 350 micrometer. In an embodiment of the invention, the average particle size of the sugar alcohol composition is less than 250 micrometer. In an embodiment of the invention, the average particle size of the sugar alcohol composition is at least 100 micrometer.

In an embodiment of the invention, the one or more cannabinoids is present in an amount of 0.5 to 100 mg.

In an embodiment of the invention, the one or more cannabinoids is present in an amount of 1 to 80 mg. In an embodiment of the invention, the one or more cannabinoids is present in an amount of 5 to 50 mg. In an embodiment of the invention, the one or more cannabinoids is present in an amount of 5 to 30 mg. In an embodiment of the invention, the one or more cannabinoids is present in an amount of 5 to 20 mg.

In some embodiments of the invention, the unit weight of the tablet composition is from about 50 mg to about 2000 mg. In some embodiments of the invention, the unit weight of the tablet composition is from about 50 mg to about 1000 mg. In some embodiments of the invention, the unit weight of the tablet composition is from about 50 mg to about 750 mg. In some embodiments of the invention, the unit weight of the tablet composition is from about 100 mg to about 750 mg. This is particularly the case when a tablet of two or more modules is made, such as when the tablet comprises a fast disintegrating module and a lozenge module.

In some embodiments of the invention, the one or more cannabinoids are present in an amount of 0.1 to 400 mg. In some embodiments of the invention, the one or more cannabinoids are present in an amount of 10 to 100 mg.

In an embodiment of the invention, the one or more cannabinoids are present in an amount of 0.1 to 200 mg. In some other embodiments of the invention, the one or more cannabinoids are present in an amount of 0.1 to 100 mg. In some other embodiments of the invention, the one or more cannabinoids are present in an amount of 0.1 to 50 mg. In an embodiment of the invention said tablet comprises said cannabinoids in an amount of 0.1-30 mg, such as 1-20 mg, such as 5-15 mg.

In an embodiment of the invention, the one or more cannabinoids comprises cannabidiol (CBD), cannabidiolic acid (CBDA), cannabidivarin (CBDV), salts and derivatives thereof.

In an embodiment of the invention, the one or more cannabinoids comprises tetrahydrocannabinol (THC), tetrahydrocannabinolic acid (THCA), tetrahydrocannabivarin (THCV), salts and derivatives thereof.

In an embodiment of the invention, the one or more cannabinoids comprises cannabidiol (CBD).

In an embodiment of the invention, the one or more cannabinoids is selected from the group consisting of cannabidiol (CBD), cannabidiolic acid (CBDA), tetrahydrocannabinol (THC), tetrahydrocannabinolic acid (THCA), cannabigerol (CBG), cannabichromene (CBC), cannabinol (CBN), cannabielsoin (CBE), iso-tetrahydrocannabinol (iso-THC), cannabicyclol (CBL), cannabicitran (CBT), cannabivarin (CBV), tetrahydrocannabivarin (THCV), cannabidivarin (CBDV), cannabichromevarin (CBCV), cannabigerovarin (CBGV), cannabigerol monomethyl ether (CBGM), salts thereof, derivatives thereof and mixtures of cannabinoids.

In an embodiment of the invention, the one or more cannabinoids comprise cannabidiol (CBD), cannabidiolic acid (CBDA), cannabidivarin (CBDV), salts and derivatives thereof. In an embodiment of the invention the one or more cannabinoids comprises CBD, salts and derivatives thereof, including analogues and homologues. In an embodiment of the invention said one or more cannabinoids comprises CBD. In an embodiment of the invention said one or more cannabinoids is CBD.

In an embodiment of the invention, the one or more cannabinoids comprise tetrahydrocannabinol (THC), tetrahydrocannabinolic acid (THCA), tetrahydrocannabivarin (THCV), salts and derivatives thereof. In an embodiment of the invention said one or more cannabinoids comprises tetrahydrocannabinol (THC). Preferably THC is intended to mean (−)-trans-$\Delta^9$-tetrahydrocannabinol, i.e. (6aR,10aR)-delta-9-tetrahydrocannabinol). In an embodiment of the invention said one or more cannabinoids is THC.

In an embodiment of the invention, the one or more cannabinoids comprise at least two cannabinoids. In an embodiment of the invention said one or more cannabinoids comprises a combination of several cannabinoids, such as THC and CBD. In an embodiment of the invention said one or more cannabinoids is a combination of THC and CBD.

In an embodiment of the invention, the tablet formulation comprises flavor in an amount between 0.01 and 10% by weight of the tablet formulation such as in an amount between 0.01 and 5% by weight of the tablet formulation.

In an embodiment of the invention, the tablet formulation comprises high intensity sweetener.

In an embodiment of the invention, the one or more cannabinoids are present in solid form. In an embodiment of the invention, the one or more cannabinoids are present in liquid or semi-liquid form.

In an embodiment of the invention, the one or more cannabinoids forms part of a complex with cyclodextrin. In an embodiment of the invention, the one or more cannabinoids form part of a complex with cyclodextrin. This complex may enhance the release of cannabinoids according to the present invention. Also, the complex may enhance delivery of the one or more cannabinoids to the oral mucosa.

In an embodiment of the invention, the one or more cannabinoids comprises at least one phytocannabinoid that forms part of an extract. In some embodiments of the invention, it was seen that cannabinoids as part of an extract may enhance the release of cannabinoids.

In an embodiment of the invention, the one or more cannabinoids comprises at least one isolated cannabinoid.

In an embodiment of the invention, the one or more cannabinoids is located in a protein carrier, such as pea protein carrier.

In an embodiment of the invention, the one or more cannabinoids is located in a polymer carrier.

In an embodiment of the invention, the one or more cannabinoids is located in an amphiphilic polymer carrier.

In an embodiment of the invention, the one or more cannabinoids comprises at least one endocannabinoid or endocannabinoid-like compound, such as palmitoylethanolamide (PEA).

In an embodiment of the invention, the one or more cannabinoids comprises at least one water-soluble cannabinoid.

In an embodiment of the invention, the tablet comprises a self-emulsifying agent.

In an embodiment of the invention, the tablet comprises a lipophilic association between the one or more cannabinoids and a fatty acid, such as oleic acid.

In an embodiment of the invention, the tablet comprises a lipid carrier for the one or more cannabinoids.

In an embodiment of the invention, the one or more cannabinoid lipid carriers comprises one or more terpenes.

In an embodiment of the invention, the one or more cannabinoid lipid carriers comprises one or more terpenes selected from the group consisting of bisabolol, borneol, caryophyllene, carene, camphene, cineol, citronella, eucalyptol, geraniol, guaiol, humulene, isopropyltoluene, isopulegol, linalool, limonene, menthol, myrcene, nerolidol, ocimene, pinene, phytol, pulegone, terpinene, terpinolene, thymol, salts thereof, derivatives thereof, and mixtures of terpenes.

In an embodiment of the invention, the tablet is used for the treatment or alleviation of a medical condition.

In certain embodiments of the invention, the tablet formulation of the present invention may be used for the treatment or alleviation of a medical condition selected from the group consisting of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia.

In another aspect of the invention, the tablet comprises a further tablet module that is different in composition.

If not stated otherwise, if the tablet according to the invention is made as one module, contrary to two or more modules, then the tablet is intended to be an FDT tablet. If on the other hand, the tablet is made of more than one module, such as two modules, such additional module is intended to be a "lozenge" module, which provides a longer disintegration time compared to the FDT module according to the invention. The combination of a "FDT" module and a "lozenge" module is addressed in the following sections and contributes to another aspect of the invention. A "lozenge" module according to the invention may also comprise elements from the "FDT" modules described in the previous sections but is generally different in composition, providing an extended disintegration time.

In an embodiment of the invention, the tablet comprises a further tablet module that is different in composition and comprises one or more cannabinoids according to the previous description of FDT elements.

In an embodiment of the invention, the tablet comprises a further tablet module that is different in composition and disintegrates within a period of 3 minutes or more in contact with oral saliva In an embodiment of the invention, the tablet comprises a further tablet module that is different in composition and disintegrates within a period of 4 minutes or more in contact with oral saliva In an embodiment of the invention, the tablet comprises a further tablet module that is different in composition and comprises a sugar alcohol composition according to the previous description of FDT elements.

In an embodiment of the invention, the tablet comprises a further tablet module that is different in composition and comprising a sugar alcohol composition having a larger average particle size.

In an embodiment of the invention, the tablet comprises a further tablet module that is different in composition and constitutes at least 50% by weight of the total tablet.

In an embodiment of the invention, the tablet comprises a further tablet module that is different in composition and constitutes at least 60% by weight of the total tablet.

In an embodiment of the invention, the tablet comprises a further tablet module that is different in composition and constitutes at least 70% by weight of the total tablet.

In an embodiment of the invention, the tablet comprises a further tablet module that is different in composition and constitutes between 50-90% by weight of the total tablet.

In an embodiment of the invention, the tablet comprises a further tablet module that is different in composition and constitutes between 60-90% by weight of the total tablet.

In an embodiment of the invention, the tablet comprises a further tablet module that is different in composition and constitutes between 70-90% by weight of the total tablet.

In an embodiment of the invention, the tablet comprises a further tablet module that is different in composition and having a unit weight from about 250 mg to about 950 mg.

In an embodiment of the invention, the tablet comprises a further tablet module that is different in composition and having a unit weight from about 400 mg to about 900 mg.

In an embodiment of the invention, the tablet comprises a further tablet module that is different in composition and having a unit weight from about 400 mg to about 900 mg.

In an embodiment of the invention, the tablet comprises a further tablet module that is different in composition and having a unit weight from about 200 mg to about 500 mg.

In an embodiment of the invention, the tablet comprises a further tablet module that is different in composition and comprises gum base polymers.

In an embodiment of the invention, the tablet comprises a further tablet module that is different in composition and does not comprise gum base polymers.

In an embodiment of the invention, the tablet comprises a further tablet module that is different in composition and is tableted together with an FDT tablet according to the previous description of FDT elements, to form an integrated two-layered tablet.

In an embodiment of the invention, the tablet comprises a further tablet module that is different in composition and is tableted in a separate step before tableting the FDT tablet according to the previous description of FDT elements.

In an embodiment of the invention, the tablet comprises a further tablet module that is different in composition and is tableted in a separate step with a higher pressure before tableting the FDT tablet according to the previous description of FDT elements.

In an embodiment of the invention, the tablet comprises a further tablet module that is different in composition and comprises any of a binder, a dissolution agent, an excipient, a viscolising agent or an alkaline buffering agent according to the previous description of FDT elements.

DETAILED DESCRIPTION OF THE INVENTION

The invention will now be described in more details with respect to certain aspects and embodiments of the invention. These aspects and embodiments are intended to be understood in connection with the rest of the description, including the Summary of the Invention and the Examples of the invention.

As used herein, the term "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

As used herein, the term "disintegrate" refers to a reduction of an object to components, fragments or particles. Disintegration time may be measured in vitro or in vivo. Unless otherwise stated, the in vitro measurements are carried out in accordance to European Pharmacopeia 9.0, section 2.9.1, Disintegration of tablets and capsules.

As used herein, the term "dissolve" is the process where a solid substance enters a solvent (oral saliva) to yield a solution. Unless otherwise stated, dissolving implies a full dissolving of the compound in question.

As used herein, the terms "disintegrant" refers to an ingredient facilitating disintegration of an FDT-module, when the FDT-module comes into contact with saliva. Disintegrants usable within the scope of the invention may include starch, pregelatinated starch, modified starch (including potato starch, maize starch, starch 1500, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, and calcium silicate. Disintegrants may often be considered as measure promoting the break-up of the module into smaller fragments upon administration to facilitate nicotine release and eventual absorption. Crospovidone may comprise various grades, such as Kollidon CL-F or Kollidon CL-SF available from BASF.

The term "disintegrant composition" is intended to mean a volume of matter comprising one or more disintegrant. The disintegrant composition may contain other excipients than disintegrants. The disintegrant composition may constitute disintegrants. The disintegrant composition may constitute one type of disintegrants. The disintegrant composition may constitute two types of disintegrants. The disintegrant composition may constitute two or more types of disintegrants. Preferably, the disintegrant composition comprises a "portion of particles". Preferably, the disintegrant composition is a "portion of particles".

The term "particle size" relates to the ability of the particles to move through or be retained by sieve holes of a specific size. As used herein, the term "particle size" refers to the average particle size as determined according to European Pharmacopoeia 9.1 when using test method 2.9.38 particle size distribution estimation by analytical sieving, unless otherwise specifically is mentioned.

The term "plurality of particles" is intended to cover the "population of particles" in the sense that the sum of populations are covered by the term "plurality".

The term "portion of particles" or similar wording is intended to mean a plurality of particles that collectively may comprise one or more populations of particles.

The term "particle" or similar wording is intended to denote a single, discrete composition of solid matter, such as a granule or individual elements in powder, having a certain size that may deviate considerable.

The term "DC sugar alcohol particles" or similar wording refers to particles of direct compressible (DC) sugar alcohol. DC sugar alcohol particles may be obtained e.g. as particles of sugar alcohols having DC grade by nature, e.g. sorbitol, or by granulating non-DC sugar alcohol with e.g. other sugar alcohols or binders for the purpose of obtaining so-called direct compressible particles (DC). Also, granulation of non-DC sugar alcohol with water as binder is considered to result in "DC sugar alcohol particles" in the present context.

This is contrary to the term "non-DC sugar alcohol particles" that refers to particles of non-directly compressible (non-DC) sugar alcohol. In the present context, the non-DC sugar alcohol particles refer to particles which have not been preprocessed by granulation with e.g. other sugar alcohols or binders for the purpose of obtaining so-called direct compressible particles (DC). Thus, non-DC sugar alcohol particles are considered as particles consisting of non-DC sugar alcohol.

The term "sugar alcohol composition" is intended to mean a volume of matter comprising one or more sugar alcohols. The disintegrant composition may contain other excipients than sugar alcohols. The sugar alcohol composition may constitute sugar alcohols. The sugar alcohol composition may constitute one type of sugar alcohols. The sugar alcohol composition may constitute two types of sugar alcohols. The sugar alcohol composition may constitute two or more types of sugar alcohols. Preferably, the sugar alcohol composition comprises a "portion of particles". Preferably, the sugar alcohol composition is a "portion of particles".

The term "tableted" or "tablet" or "compressed" is intended to mean that the tablet composition is pressed in a tableting apparatus and mainly being composed of particulate matter. Although the terms imply a method step, in the present context, the terms are intended to mean the resulting tablet obtained in tableting a portion of particles. It is noted that a tablet or tableted composition that is mentioned to comprise particles eventually is to be understood as particles that have been pressed together in a tableting step.

In one aspect of the invention, the "tablet" is intended to mean a "fast disintegrating tablet" ("FDT"), or similar wording, such as "orally disintegrating tablet" ("ODT"). If not stated otherwise, if the tablet according to the invention is made as one module, contrary to two or more modules, then the tablet is intended to be an FDT tablet. If on the other hand, the tablet is made of more than one module, such as two modules, such additional module is intended to be a "lozenge" module, which provides a longer disintegration time compared to the FDT module according to the invention. The combination of an "FDT" module and a "lozenge" module contributes to another aspect of the invention. A "lozenge" module according to the invention may also comprise elements from the "FDT" modules but is generally different in composition, providing an extended disintegration time.

The term "lozenge" is intended to cover that a "lozenge composition" has been "compressed" into a "lozenge module". In the present context, a "lozenge module" or similar wording is intended to mean that the module during use in the oral cavity is intended to be sucked or licked on. The term "lozenge" is given the ordinary meaning in the art of lozenges. The intention is that the lozenge module may not be chewed. The intention is also that the FDT module may not be chewed. Generally, the "lozenge module" of the present invention may disintegrate upon sucking or licked in minutes, contrary to seconds for orally disintegrating tablets (ODT) or fast disintegrating tablets (FDT) tablets. Hence, the intention is that the "lozenge module" is to deliver the one or more cannabinoids over a longer period of time than the FDT module, if the tablet is made as a combination of the two modules.

The term "module" is generally intended to be composed of a composition of matter with substantially the same characteristics throughout the module. Hence, if two module are present, then the two modules are different in composition and generally have two different characteristics throughout each module. In the present context, if only one module is present, then this module is considered an FDT tablet. On the other hand, if two modules are present, then the tablet is composed of an FDT tablet or FDT tablet module fused with a lozenge tablet or lozenge module. The term "fused" is intended to mean that the tablet is gathered together by means of compression force. Usually, if two modules are present, the lozenge module is made as the first module and the FDT module is made as the second module. The tablet may be composed of more than two module. The lozenge module may in certain embodiments be replaced by a gum base module. In the present context, the invention provides an attractive bi-phasic delivery of masking, even if the delivery of nicotine is "single-phased".

The wording "a further tablet module that is different in composition" or similar wordings is intended to mean that this further module is distinguished from the FDT module in the sense that the composition of the module is substantially different from the FDT module, such as with respect to disintegration time.

The term "cannabinoid composition" is intended to mean a volume of matter comprising one or more cannabinoids. The cannabinoid composition may contain other components than cannabinoids. The cannabinoid composition may constitute cannabinoids. The cannabinoid composition may constitute one type of cannabinoids. The cannabinoid composition may constitute two types of cannabinoids. The cannabinoid composition may constitute two or more types of cannabinoids.

The term "weight of the tablet composition" or similar wording meaning the same is defined in the present context as weight of the tablet composition, not including the weight of an outer coating, such as a hard coating, soft coating, and the like.

By the phrase "texture" is meant a qualitative measure of the properties of the tablet composition or tablet and of the overall mouth feel experienced by the user during use. Thus, the term "texture" encompasses measurable quantities such as hardness as well as more subjective parameters related to the feel experienced by a user.

The term "in vivo use" intends to mean that the tablet composition system is used by a human subject in an experimental setup of trained test persons according to statistically principles and that either the saliva of the human subject is subject to measurements or the tablet composition is subject to measurements.

The term "in vivo release" or "in vivo testing of release" or similar wording intends to mean that the tablet composition is tested as outlined in the examples.

The term "in vitro release" or "in vitro testing of release" or similar wording intends to mean that the tablet composition is tested according to the examples.

The term "release" in the present context is intended to mean under "in vitro" conditions if not stated otherwise. In particular, the "release rate" during a certain period of time is intended to mean the amount in percentage of cannabinoids that is released during the period.

The term "sustained release" or "extended release" is herein intended to mean prolonged release over time. The term "rapid release" or "quick release" or "high release" is herein intended to mean a higher content released for a given period of time. The term "controlled release" is intended to mean a release of a substance from a tablet composition by the aid of active use of the tablet composition in the oral cavity of the subject, whereby the active use is controlling the amount of substance released.

The term "delivery to the oral mucosa" or similar wording intends to mean that the tablet composition is tested according to the examples.

As used herein, the term "buffering agent" is used interchangeably with "buffer" and refers to agents for obtaining a buffer solution. Buffering agents include acidic buffering agents, i.e. for obtaining a buffer solution with an acidic pH, and alkaline buffering agents, i.e. for obtaining a buffer solution with an alkaline pH.

A "self-emulsifying agent" is an agent which will form an emulsion when presented with an alternate phase with a minimum energy requirement. In contrast, an emulsifying agent, as opposed to a self-emulsifying agent, is one requiring additional energy to form an emulsion.

In an embodiment of the invention, the tablet composition comprises further tablet composition ingredients selected from the group consisting of flavors, dry-binders, tableting aids, anti-caking agents, emulsifiers, antioxidants, enhancers, mucoadhesives, absorption enhancers, high intensity sweeteners, softeners, colors, active ingredients, water-soluble indigestible polysaccharides, water-insoluble polysaccharides or any combination thereof.

In embodiments where the lozenge comprises fillers, different fillers may be used. Microcrystalline cellulose may be used as a filler in some embodiments of the invention. Examples of usable fillers include magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, starch polymers, fibers and combinations thereof.

Examples of usable disintegrants include starch, pregelatinated starch, modified starch (including potato starch, maize starch, starch 1500, sodium starch glycolate and starch derivatives), cellulose, microcrystalline cellulose, alginates, ion-exchange resin, and superdisintegrants, such as crospovidone, croscarmellose sodium, and sodium starch glycolate, crosslinked cellulose (such as sodium carboxy methyl cellulose), crosslinked polyvinyl pyrrolidone (PVP), crosslinked starch, crosslinked alginic acid, natural superdisintegrants, and calcium silicate, and combinations thereof.

Usable high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), cinnamon redhots, cotton candy, circus cotton candy, clove, coconut, coffee, clear coffee, double chocolate, energy cow, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

Usable buffering agents include carbonate, including monocarbonate, bicarbonate and sesquicarbonate, glycerinate, phosphate, glycerophosphate, acetate, gluconate or citrate of an alkali metal, ammonium, tris buffer, amino acids and mixtures thereof. Encapsulated buffer such as Effersoda may also be used.

In some embodiments, the buffering agent comprises sodium carbonate and sodium bicarbonate, e.g. in a weight-ratio between 5:1 and 2.5:1, preferably in a weight-ratio between 4.1:1 and 3.5:1.

Silicon dioxide may be used as a glidant. Other glidants usable for the formulation may also be used within the scope of the invention. Magnesium stearate and/or sodium stearyl fumerate may be used as a lubricant. Other lubricants usable for the formulation may also be used within the scope of the invention.

Ready to use systems may be used within the scope of the invention. Typically, such ready-to-use systems may e.g. replace filler, disintegrant, glidant or similar with a single powder mix. Suitable ready-to-use systems for the purpose, but not limited to, include Pearlitol Flash (Roquette), Pharmaburst 500 (SPI Pharma), Ludiflash (BASF), ProSolv (JRS Pharma), ProSolv EasyTab (JRS Pharma), F-Melt (Fuji Chemical), SmartEx50 or SmartEx100 (Shin Etsu/Harke Pharma). Using a ready to use systems comprising a disintegrant may be especially advantageous.

Particularly, including a disintegrant may significantly influence the disintegration time, subject to the total composition of the second module. Also, by varying the amount and type of the disintegrant, the disintegration time may be further adjusted. For example, if the second layer having a lower disintegration time is desired, the percentage content of disintegrant may be increased and/or the type of disintegrant may be at least partly exchanged for a more effective disintegrant.

Also, decreasing the particle size of the disintegrant tends to lower the disintegration time, likely due to an increased surface area to volume ratio.

Furthermore, the compression force used to press the second module correlate significantly with the obtained hardness of the second module, such that a high compression force typically increases the hardness of the obtained second module. By adjusting the hardness of a second module, the disintegration time may also be influenced, such that a lowered hardness typically gives a shorter disintegration time. Here it has been observed for a number of compositions that by applying the correct compression force a disintegration time below 60 seconds upon oral administration can be achieved, whereas a too high compression force may result in a longer disintegration time above 60 seconds. In this regard it is noted that the threshold compression force may vary significantly, depending on other parameters, such as overall composition, content and type of disintegrant, etc. When, for example, a certain setup results in a too slow disintegration, a further way of adjusting may be to replace a regular disintegrant with a superdisintegrant, i.e. which facilitates disintegration in a more efficient way.

Typically, the formulation of the FDT module may comprise ingredients selected from the group consisting of bulk sweeteners, fillers, ready to use systems, flavors, dry-binders, disintegrant, hereunder superdisintegrants, tabletting aids, anti-caking agents, emulsifiers, antioxidants, enhancers, absorption enhancers, buffering agents, high intensity sweeteners, colors, glidants, lubricants, or any combination thereof. Absorption enhancers may include e.g. pH regulating agents, such as buffering agents, and mucoadhesive.

Mannitol may be used as the sugar alcohol in the lozenge module and FDT module. Particularly preferred mannitol grades include mannitol 100 SD, mannitol 150 SD or mannitol 200 SD commercially available from Roquette with different average particle sizes. Other usable sugar alcohols for use in the lozenge module may include sorbitol, erythritol, xylitol, maltitol, lactitol, and isomalt. Of these isomalt, erythritol, and sorbitol are particularly preferred. Other usable sugar alcohols for use in the FDT module may include sorbitol, erythritol, xylitol, maltitol, lactitol, and isomalt. The disintegrant in FDT module may e.g. be a starch based disintegrant. In embodiments of the invention, the disintegrant may be supplied as part of a ready to use system, e.g. Pearlitol Flash from Roquette, a mannitol-based product comprising approximately 17% by weight of disintegrant. Examples of other usable ready to use system include e.g. Pharmaburst 500 (SPI Pharma), Ludiflash (BASF), ProSolv (JRS Pharma), ProSolv EasyTab (JRS Pharma), F-Melt (Fuji Chemical), SmartEx50 or SmartEx100 (Shin Etsu/Harke Pharma).

Pearlitol Flash is used comprising approximately 17% by weight of starch disintegrant. Examples of other usable ready to use system include e.g. Pharmaburst 500 (SPI Pharma), Ludiflash (BASF), ProSolv (JRS Pharma), ProSolv EasyTab (JRS Pharma), F-Melt (Fuji Chemical), SmartEx50 or SmartEx100 (Shin Etsu/Harke Pharma).

Preferred high intensity sweeteners (HIS) may e.g. be sucralose, acesulfame potassium, and mixtures thereof. Other high intensity sweeteners, such as aspartame, salts of acesulfame, such as acesulfame potassium, alitame, saccharin and its salts, cyclamic acid and its salts, glycyrrhizin, dihydrochalcones, thaumatin, monellin, stevioside, alone or in combination, are also usable within the scope of the invention.

Menthol, peppermint, and mixtures thereof may be used in the above formulations as flavors. Other flavors may also be used within the scope of the invention.

Sodium carbonate may be used as the buffer. Further usable buffers include other carbonates, including monocarbonates, bicarbonates and sesquicarbonates, glycerinate, phosphate, glycerophosphate, acetate, glyconate or citrate of an alkali metal, ammonium, tris buffer, amino acids and mixtures thereof.

In the above MgSt (Magnesium stearate) is used as lubricant. Other lubricants, such as sodium stearyl fumerate may also be usable within the scope of the invention.

According to embodiments of the invention, emulsifiers may be selected from the group consisting of sucrose ester of fatty acids (such as sucrose mono stearate), polyethylene glycol esters or ethers (PEG) (such as caprylocaproyl macrogol-8 glycerides and lauroyl macrogol-32-glycerides), mono- and diglyceride of fatty acids (such as glycerol monostearate, glycerol monolaurate, glyceryl behenate ester), acetic acid esters of mono- and diglycerides of fatty acids (Acetem), polyoxyethylene alkyl ethers, diacetyl tartaric ester of monoglycerides, lactylated monoglycerides, glycerophospholipids (such as lecithin), poloxamer (non-ionic block copolymer of ethylene oxide and propylene oxide), cyclodextrins, fatty acid esters of sorbitol (such as sorbitan monolaurate, sorbitan monostearate, sorbitan tristearate, polysorbates). Self-emulsifying emulsifiers may be phospholipids (Lecithin), Polysorbates (polysorbate 80).

SEDDS (self-emulsifying drug delivery system) may consist of hard or soft capsules filled with a liquid or a gel that consists of self-emulsifiers, one or more cannabinoids, oil (to dissolve the cannabinoids) and a surfactant. SEDDS may comprise of a blend or mixture of self-emulsifiers, one or more cannabinoids, oil (to dissolve the cannabinoids) and a surfactant. SEDDS may comprise granules comprising self-emulsifiers, one or more cannabinoids, oil (to dissolve the cannabinoids), one or more surfactants, solvent and co-solvents. Upon contact with gastric fluid, the SEDDS spontaneously emulsify due to the presence of surfactants. Many surfactants, however, are lipid based and interact with lipases in the GIT (gastro intestinal tract). This can lead to a reduced capability of the lipid-based surfactants to emulsify the one or more cannabinoids as well as the oil carrier, both reducing bioavailability.

In the present context, SEDDS is a solid or liquid dosage form comprising an oil phase, a surfactant and optionally a co-surfactant, characterized primarily in that said dosage form can form oil-in-water emulsion spontaneously in the oral cavity or at ambient temperature (referring generally to body temperature, namely 37° C.) with mild stirring. When a SEDDS enters the oral cavity, it is initially self-emulsified as emulsion droplets and rapidly dispersed throughout the oral cavity, and thus reducing the irritation caused by the direct contact of the drug with the mucous membrane of the oral cavity. In the oral cavity, the structure of the emulsion microparticulate will be changed or destroyed. The resulting microparticulate of micrometer or nanometer level can penetrate into the mucous membrane of the oral cavity, and the digested oil droplets enter the blood circulation, thereby significantly improving the bioavailability of the drug.

Particularly with respect to SEDDS, the formulation of the present invention may provide some clear benefits, both allowing a higher load of cannabinoids and at the same time offer improved sensorics properties of the formulation during use. Other advantages are also present. Compared to prior art formulations, it is believed that the combination of the component where the one or more cannabinoids are associated and the composition comprising one or more sugar alcohol particles provides the benefits of the present invention both with respect to loading of cannabinoids and improved sensorics properties, such as less off-notes.

In an embodiment of the invention, the one or more self-emulsifiers are selected from the group consisting of PEG-35 castor oil, PEG-6 oleoyl glycerides, PEG-6 linoleoyl glycerides, PEG-8 caprylic/capric glyceride, sorbitan monolaurate, sorbitan monooleate, polyoxyethylene (20) sorbitan monolaurate, polyoxyethylene (60) sorbitan monostearate, polyoxyethylene (80) sorbitan monooleate, lauroylpoloxyl-32 glycerides, stearoyl polyoxyl-32 glycerides, polyoxyl-32 stearate, propylene glycol mono laurate, propylene glycol di laurate, and mixtures and combinations thereof.

According to embodiments of the invention, flavors may be selected from the group consisting of coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

Petroleum waxes aid in the curing of the finished tablet composition made from the tablet composition as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavors escape from this wax versus a wax having larger crystal sizes.

Petroleum wax (refined paraffin and microcrystalline wax) and paraffin wax are composed of mainly straight-chained normal-alkanes and branched iso-alkanes. The ratio of normal-alkanes to iso-alkanes varies.

Microcrystalline cellulose may be applied in various grades, such as Avicel PH-101, Avicel PH-102 or Avicel PH-105 commercially available from FMC.

Antioxidants prolong shelf life and storage of tablet composition, finished tablet composition or their respective components including fats and flavor oils.

Antioxidants suitable for use in tablet composition include butylated hydroxyanisole (BHA), butylated hydroxytoluene (BHT), betacarotenes, tocopherols, acidulants such as Vitamin C (ascorbic acid or corresponding salts (ascorbates)), propyl gallate, catechins, other synthetic and natural types or mixtures thereof.

Further tablet composition ingredients, which may be included in the tablet composition according to the present invention, include surfactants and/or solubilizers. As examples of types of surfactants to be used as solubilizers in a tablet composition according to the invention, reference is made to H. P. Fiedler, Lexikon der Hilfstoffe für Pharmacie, Kosmetik and Angrenzende Gebiete, pages 63-64 (1981) and the lists of approved food emulsifiers of the individual countries. Anionic, cationic, amphoteric or non-ionic solubilizers can be used. Suitable solubilizers include lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene sorbitan fatty acid esters, sorbitan esters of fatty acids and polyoxyethylene steraric acid esters.

Particularly suitable solubilizers are polyoxyethylene stearates, such as for instance polyoxyethylene(8)stearate and polyoxyethylene(40)stearate, the polyoxyethylene sorbitan fatty acid esters sold under the trade name TWEEN, for instance TWEEN 20 (monolaurate), TWEEN 80 (monooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, block-copolymers of ethylene oxide and propyleneoxide and polyoxyethylene fatty alcohol ether. The solubilizer may either be a single compound or a combination of several compounds. In the presence of an active ingredient, such as the included one or more cannabinoids, the tablet composition may preferably also comprise a carrier known in the arts of tablet composition and active ingredients. Poloxamer F68 is a further highly suitable solubilizer.

High intensity artificial sweetening agents can also be used according to preferred embodiments of the invention. Preferred high intensity sweeteners include, but are not limited to sucralose, aspartame, salts of acesulfame, alitame, neotame, saccharin and its salts, cyclamic acid and its salts, glycyrrhizin, dihydrochalcones, thaumatin, monellin, monk fruit extract, advantame, stevioside and the like, alone or in combination.

In order to provide longer lasting sweetness and flavor perception, it may be desirable to encapsulate or otherwise control the release of at least a portion of the artificial sweeteners.

Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet composition component such as a resinous compound.

Usage level of the high-intensity sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated high-intensity sweetener will be proportionately higher.

A tablet composition and/or lozenge composition may, if desired, include one or more fillers/texturizers including as examples, magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, and combinations thereof. According to an embodiment of the invention, one preferred filler/texturizer is calcium carbonate.

A number of tablet composition components well known within the art may be applied within the scope of the present invention. Such components comprise but are not limited to waxes, fats, softeners, fillers, bulk sweeteners, flavors, antioxidants, emulsifiers, coloring agents, binding agents and acidulants.

In an embodiment of the invention, water-soluble ingredients comprise at least one sugar alcohol. The at least one sugar alcohol may be selected from the group consisting of xylitol, sorbitol, mannitol, maltitol, isomaltitol, isomalt, erythritol, lactitol, maltodextrin, hydrogenated starch hydrolysates, and combinations thereof.

In an aspect of the invention, the sugar alcohol of the invention may be replaced by one or more sugars, such as a sugar selected from the group consisting of dextrose, sucrose, maltose, fructose, lactose, and combinations thereof.

Sugar sweeteners generally include, but are not limited to saccharide-containing components, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

The tablet according to the invention is manufactured by applying pressure to a content of particles by suitable compression means. The particles or powder is then pressed into a compact coherent tablet. The particles may for example comprise so-called primary particles or aggregated primary particles. When these are pressed, bonds are established between the particles or granules, thereby conferring a certain mechanical strength to the pressed tablet.

It should be noted that the above-introduced terms: powder, primary particles and aggregated primary particles may be somewhat misleading in the sense that the difference between primary particles and aggregated primary particles may very often be looked upon differently depending on the background of the user. Some may for instance regard a sweetener, such as sorbitol, as a primary particle in spite of the fact that sorbitol due to the typically preprocessing performed on sorbitol when delivered to the customer should rather be regarded as some sort of aggregated primary particles. The definition adopted in the description of this invention is that aggregated primary particles refer to macro-particles comprising more or less preprocessed primary particles.

When pressure is applied to the particles, the bulk volume is reduced, and the amount of air is decreased. During this process energy is consumed. As the particles come into closer proximity to each other during the volume reduction process, bonds may be established between the particles or granules. The formation of bonds is associated with a reduction in the energy of the system as energy is released. Volume reduction takes place by various mechanisms and different types of bonds may be established between the particles or granules depending on the pressure applied and the properties of the particles or granules. The first thing that happens when a powder is pressed is that the particles are rearranged under low compaction pressures to form a closer packing structure. Particles with a regular shape appear to undergo rearrangement more easily than those of irregular shape. As the pressure increases, further rearrangement is prevented, and subsequent volume reduction is obtained by plastic and elastic deformation and/or fragmentation of the tablet particles. Brittle particles are likely to undergo fragmentation, i.e. breakage of the original particles into smaller units. Plastic deformation is an irreversible process resulting in a permanent change of particle shape, whereas the particles resume their original shape after elastic deformation. Evidently, both plastic and elastic deformation may occur, when compressing a tablet composition.

By the method of the invention, it is possible to form one-layered or multi-layered tablets, such as two-layered tablets or three-layered tablets.

Several studies of the bond types in pressed tablets have been made over the years, typically in the context of pharmaceuticals and several techniques of obtaining pressed tablets on the basis of available powders has been provided. Such studies have been quite focused on what happens when the volume reduction is performed and how the end-product may be optimized for the given purpose. Several refinements with respect to pressed tablets has for instance been made in the addition of for example binders in the tablet raw materials for the purpose of obtaining a sufficient strength to the final pressed tablet while maintaining acceptable properties, e.g. with respect to release.

In accordance with the invention, the tableted tablet composition according to the invention may comprise about 0.1 to about 75% by weight of an outer coating applied onto the tablet composition centre. Thus, suitable coating types include hard coatings, film coatings and soft coatings of any composition including those currently used in coating of tableted tablet composition.

One presently preferred outer coating type is a hard coating, which term is used in the conventional meaning of that term including sugar coatings and sugar-free (or sugarless) coatings and combinations thereof. The object of hard coating is to obtain a sweet, crunchy layer, which is appreciated by the consumer and it may moreover protect the tablet composition centres for various reasons. In a typical process of providing the tablet composition centres with a protective sugar coating, the tablet composition centres are successively treated in suitable coating equipment with aqueous solutions of crystallisable sugar such as sucrose or dextrose, which, depending on the stage of coating reached, may contain other functional ingredients, e.g. fillers, binding agents, colours, etc. In the present context, the sugar coating may contain further functional or active compounds including flavour compounds and/or active compounds.

In a typical hard coating process as it will be described in detail in the following, a suspension containing crystallisable sugar and/or polyol is applied onto the tablet composition centres and the water it contains is evaporated off by blowing with air. This cycle must be repeated several times, typically 3 to 80 times, in order to reach the swelling required. The term "swelling" refers to the increase in weight or thickness of the products, as considered at the end of the coating operation by comparison with the beginning, and in relation to the final weight or thickness of the coated products. In accordance with the present invention, the coating layer constitutes about 0.1 to about 75% by weight of the finished tablet composition element, such as about 10 to about 60% by weight, including about 15 to about 50% by weight.

In further useful embodiments, the outer coating of the tablet composition element of the invention is an element that is subjected to a film coating process and which therefore comprises one or more film-forming polymeric agents and optionally one or more auxiliary compounds, e.g. plasticizers, pigments and opacifiers. A film coating is a thin polymer-based coating applied to a tablet composition centre of any of the above forms. The thickness of such a coating is usually between 20 and 100 µm.

Generally, the film coating is obtained by passing the tablet composition centres through a spray zone with atomized droplets of the coating materials in a suitable aqueous or organic solvent vehicle, after which the material adhering to the tablet composition centres is dried before the next portion of coating is received. This cycle is repeated until the coating is complete.

In the present context, suitable film-coating polymers include edible cellulose derivatives such as cellulose ethers including methylcellulose (MC), hydroxyethyl cellulose (HEC), hydroxypropyl cellulose (HPC) and hydroxypropyl methylcellulose (HPMC). Other useful film-coating agents are acrylic polymers and copolymers, e.g. methylacrylate aminoester copolymer or mixtures of cellulose derivatives and acrylic polymers. A particular group of film-coating polymers, also referred to as functional polymers are polymers that, in addition to its film-forming characteristics, confer a modified release performance with respect to active components of the tablet composition formulation. Such release modifying polymers include methylacrylate ester copolymers, ethylcellulose (EC) and enteric polymers designed to resist the acidic stomach environment. The latter group of polymers include: cellulose acetate phtalate (CAP), polyvinyl acetate phtalate (PVAP), shellac, metacrylic acid copolymers, cellulose acetate trimellitate (CAT) and HPMC.

It will be appreciated that the outer film coating according to the present invention may comprise any combination of the above film-coating polymers.

According to the invention, the one or more cannabinoids may be selected from various cannabinoids.

"Cannabinoids" are a group of compounds including the endocannabinoids, the phytocannabinoids and those which are neither endocannabinoids or phytocannabinoids, hereinafter "syntho-cannabinoids".

"Endocannabinoids" are endogenous cannabinoids, which may have high affinity ligands of CB1 and CB2 receptors.

"Phytocannabinoids" are cannabinoids that originate in nature and can be found in the *Cannabis* plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the *Cannabis* plant. Examples include WIN 55212 and rimonabant.

An "isolated phytocannabinoid" is one which has been extracted from the *Cannabis* plant and purified to such an extent that the additional components such as secondary and minor cannabinoids and the non-cannabinoid fraction have been substantially removed.

A "synthetic cannabinoid" is one which has been produced by chemical synthesis. This term includes modifying an isolated phytocannabinoid, by, for example, forming a pharmaceutically acceptable salt thereof.

A "substantially pure" cannabinoid is defined as a cannabinoid which is present at greater than 95% (w/w) pure. More preferably greater than 96% (w/w) through 97% (w/w) thorough 98% (w/w) to 99% % (w/w) and greater.

A "highly purified" cannabinoid is defined as a cannabinoid that has been extracted from the *Cannabis* plant and purified to the extent that other cannabinoids and non-cannabinoid components that are co-extracted with the cannabinoids have been substantially removed, such that the highly purified cannabinoid is greater than or equal to 95% (w/w) pure.

"Plant material" is defined as a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Center for Drug Evaluation and Research.

In the context of this application the terms "cannabinoid extract" or "extract of cannabinoids", which are used interchangeably, encompass "Botanical Drug Substances" derived from *Cannabis* plant material. A Botanical Drug Substance is defined in the Guidance for Industry Botanical Drug Products Draft Guidance, August 2000, US Department of Health and Human Services, Food and Drug Administration Centre for Drug Evaluation and Research as: "A drug substance derived from one or more plants, algae, or macroscopic fungi. It is prepared from botanical raw materials by one or more of the following processes: pulverisation, decoction, expression, aqueous extraction, ethanolic extraction, or other similar processes." A botanical drug substance does not include a highly purified or chemically modified substance derived from natural sources. Thus, in the case of *Cannabis*, "botanical drug substances" derived from *Cannabis* plants do not include highly purified, Pharmacopoeial grade cannabinoids.

The term "*Cannabis* plant(s)" encompasses wild type *Cannabis sativa* and also variants thereof, including *Cannabis* chemovars which naturally contain different amounts of the individual cannabinoids, *Cannabis sativa* subspecies *indica* including the variants var. *indica* and var. *kafiristanica, Cannabis indica, Cannabis ruderalis* and also plants which are the result of genetic crosses, self-crosses or hybrids thereof. The term "*Cannabis* plant material" is to be interpreted accordingly as encompassing plant material derived from one or more *Cannabis* plants. For the avoidance of doubt it is hereby stated that "*Cannabis* plant material" includes dried *Cannabis* biomass.

Preferably the one or more cannabinoids are selected from: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC. This list is not exhaustive and merely details the cannabinoids which are identified in the present application for reference.

So far, more than 120 different phytocannabinoids have been identified which are within the scope of the present invention.

Cannabinoids can be split into different groups as follows: Phytocannabinoids; Endocannabinoids; and Synthetic cannabinoids.

Cannabinoid receptors can be activated by three major groups of agonist ligands, for the purposes of the present invention and whether or not explicitly denominated as such herein, lipophilic in nature and classed respectively as: endocannabinoids (produced endogenously by mammalian cells); phytocannabinoids (such as cannabidiol, produced by the *Cannabis* plant); and, synthetic cannabinoids (such as HU-210).

Phytocannabinoids can be found as either the neutral carboxylic acid form or the decarboxylated form depending on the method used to extract the cannabinoids. For example, it is known that heating the carboxylic acid form will cause most of the carboxylic acid form to decarboxylate.

Phytocannabinoids can also occur as either the pentyl (5 carbon atoms) or propyl (3 carbon atoms) variant. For example, the phytocannabinoid THC is known to be a CB1 receptor agonist whereas the propyl variant THCV has been discovered to be a CB1 receptor antagonist meaning that it has almost opposite effects.

According to the invention, examples of phytocannabinoids may be cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC.

The formulation according to the present invention may also comprise at least one cannabinoid selected from those disclosed in A. Douglas Kinghorn et al., Phytocannabinoids, Vol. 103, Chapter 1, pages 1-30.

Examples of endocannabinoids are molecules that activate the cannabinoid receptors within the body. Examples include 2-arachidonyl glycerol (2AG), 2-arachidonyl glyceryl ether (2AGE), arachidonyl dopamine, and arachidonyl ethanolamide (anandamide). Structurally related endogenous molecules have been identified that share similar structural features, but that display weak or no activity towards the cannabinoid receptors but are also termed endocannabinoids. Examples of these endocannabinoid lipids include 2-acyl glycerols, alkyl or alkenyl glyceryl ethers, acyl dopamines and N-acylethanolamides that contain alternative fatty acid or alcohol moieties, as well as other fatty acid amides containing different head groups. These include N-acylserines as well as many other N-acylated amino acids. Examples of cannabinoid receptor agonists are neuromodulatory and affect short-term memory, appetite, stress response, anxiety, immune function and analgesia.

In one embodiment the cannabinoid is palmitoylethanolamide (PEA) which is an endogenous fatty acid amide belonging to the class of nuclear factor agonists.

Synthetic cannabinoids encompass a variety of distinct chemical classes: the cannabinoids structurally related to THC, the cannabinoids not related to THC, such as (cannabimimetics) including the aminoalkylindoles, 1,5-diarylpyrazoles, quinolines, and arylsulfonamides, and eicosanoids related to the endocannabinoids. All or any of these cannabinoids can be used in the present invention.

It is preferred that the formulation comprises one or two primary cannabinoids, which are preferably selected from the group consisting of, cannabidiol (CBD) or cannabidivarin (CBDV), tetrahydrocannabinol (THC), tetrahydrocannabivarin (THCV), tetrahydrocannabinolic acid (THCA), cannabigerol (CBG) and cannabidiolic acid (CBDA) or a combination thereof. It is preferred that the formulation comprises cannabidiol and/or tetrahydrocannabinol.

Preferably, the tablet composition of the present invention may be used for the treatment or alleviation of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia.

In a further aspect of the present invention the oral cannabinoid formulation is suitable for use in the treatment of conditions requiring the administration of a neuroprotectant or anti-convulsive medication.

The oral cannabinoid formulation may be for use in the treatment of seizures.

The oral cannabinoid formulation may be for use in the treatment of Dravet syndrome, Lennox Gastaut syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumours, neuropathic pain, *Cannabis* use disorder, post-traumatic stress disorder, anxiety, early psychosis, Alzheimer's disease, and autism.

The following non-limiting examples illustrate different variations of the present invention. The examples are meant for indicating the inventive concept; hence the mentioned examples should not be understood as exhaustive for the present. In particular, CBD is used as an exemplary compound, but may also be another cannabinoid.

EXAMPLES

Example 1

Component with CBD Extract 50%

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on top of one or more sugar alcohol particles. After mixing until CBD was homogeneously distributed in the one or more sugar alcohol particles, the mixture was sieved through a 1400 microns sieve.

Example 2

Component with CBD Extract 10%

CBD extract with a 10% content of CBD provided by Medical Hemp (batch number MH131B Gold), was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on top of one or more sugar alcohol particles. After mixing until CBD was homogeneously distributed in the one or more sugar alcohol particles, the mixture was sieved through a 1400 microns sieve.

Example 3

Component with CBD Isolate with a Solvent

CBD isolate from *Cannabis* plant tissues (phytocannabinoid) with a 98.5% content of CBD provided by Medical Hemp (batch number MH18212) was dissolved in a 96% ethanol solution. The ratio between the CBD isolate and ethanol was 1:1. Once CBD was dissolved in ethanol, the CBD isolate was applied in a premix with one or more sugar alcohol particles. After mixing until CBD was homogeneously distributed in the one or more sugar alcohol particles, the mixture was sieved through a 1400 microns sieve.

Example 4

Component with CBD Isolate without a Solvent

CBD isolate from *Cannabis* plant tissues (phytocannabinoid) with a 98.5% content of CBD provided by Medical Hemp (batch number MH18212) was added as free powder and mixed with one or more sugar alcohol particles. After mixing until CBD was homogeneously distributed in the one or more sugar alcohol particles, the mixture was sieved through a 1400 microns sieve.

Example 5

Component Including Microcrystalline Cellulose

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on microcrystalline cellulose (MCC). Mixing was conducted until the CBD was homogeneously distributed in the MCC. Optionally, the CBD-MCC premix could be further mixed with one or more sugar alcohol particles. The mixture was sieved through a 1400 microns sieve.

Example 6

Component Including Silicium Dioxide Carrier

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on silicium dioxide (SiO2). Mixing was conducted until the CBD was homogeneously distributed in the SiO2. Optionally, the CBD-SiO2 premix could be further mixed with one or more sugar alcohol particles. The mixture was sieved through a 1400 microns sieve.

Example 7

Component Including Hyperporous Silica Magnesium-Alumino-Metasilicates

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on hyperporous silica magnesium-alumino-metasilicates. Mixing was conducted until the CBD was homogeneously distributed in the hyperporous silica magnesium-alumino-metasilicates. Optionally, the CBD-hyperporous silica magnesium-alumino-metasilicates premix could be further mixed with one or more sugar alcohol particles. The mixture was sieved through a 1400 microns sieve.

Example 8

Preparation of Cannabinoid Component with Emulsifier and Oil

Solution of Labrafil M 1944 CS and Maisine CC (1:1) was mixed. CBD isolate from Example 3 or CBD extract from Example 1 was added and dissolved in the solution to obtain a 33% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 9

Preparation of Cannabinoid Component with Emulsifier, Oil and Co-Solvent

Solution of 60% Labrafac Lipophile WL1349 and 25% Labrasol and 15% Propylene Glycol was mixed. CBD isolate from Example 3 or CBD extract from Example 1 was added and dissolved in the solution to obtain a 33% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 10

Preparation of Cannabinoid Component with Solid Solubilizer

Gelucire 50/13 was melted at app. 60° C. and CBD isolate from Example 3 or CBD extract from Example 1 was added and dissolved in the melted solution to obtain a 50% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 11

Preparation of Cannabinoid Component with Emulsifier and Co-Solvent

CBD extract from Example 1 was preheated at 60° C., until it was in liquid form and then dissolved in Propylene Glycol. Labrasol ALF was then added to obtain a 17% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 12

Preparation of Cannabinoid Component with an Amphiphilic Polymer Carrier

CBD extract from Example 1 was preheated at 60° C. until it was in liquid form. After the preheating process, the extract was applied in a premix with Soluplus (graft-co-polymer provided by BASF) and mixed until the premix was homogeneous, obtaining a 12.5% premix of CBD. The premix was then mixed with one or more sugar alcohols. After mixing until CBD was homogeneously distributed in the one or more sugar alcohols, the mixture was sieved through a 1400 microns sieve.

Example 13

Preparation of Cannabinoid Component with Cyclodextrin and Emulsifier

CBD isolate from Example 3 was added and dissolved in polysorbate 80 to obtain a 10% solution of CBD. The 10% CBD solution was slowly added and mixed into a solution with 4% cyclodextrin to form a CBD-cyclodextrin complex. The water was removed, whereupon the complex was applied in a premix with one or more sugar alcohols. After mixing until the CBD-cyclodextrin complex was homogeneously distributed in the one or more sugar alcohols, the mixture was sieved through a 1400 microns sieve.

Example 14

A: Preparation of Fast Disintegrating Tablet (FDT) with One Layer

A cannabinoid component from either one of Examples 1 to 13 and FDT components were blended in a mixing container at about 7-9 rpm and optionally loaded with processing aid in order to improve free-flowing properties of the particles and to avoid stickiness.

In a first step, half the FDT components were added to a mixing container. High-intensity sweetener (HIS), flavors and the cannabinoid component were added to the container, after which the other half of the FDT components were added. Optionally, a premix of cannabinoids was applied. The mixture was tumbled at 7-9 rpm for 10 minutes. A processing aid was added and the mixture was tumbled at 7-9 rpm for another 2 minute. Hereafter, the mixture was ready for tableting.

FDT components include sugar alcohol particles, such as mannitol particles. Mannitol applied according to the examples was mannitol 200 SD commercially available from Roquette with different average particle sizes. Isomalt particles applied according to the examples was GalenIQ 720 commercially available from Beneo. Microcrystalline cellulose applied according to the examples was Avicel PH-105 commercially available from FMC. FDT components also include one or more disintegrants. Here crospovidone was applied in a grade available as Kollidon CL-SF available from BASF).

The mixture was subsequently led to a standard tablet pressing machine (3090i, available from Fette GmbH) comprising dosing apparatus (P 3200 C, available from Fette GmbH, Germany) and pressed into FDT tablets. The tablets were pressed using a pressing pressure of 15-20 kN. There were 75 punches on the rotor, and the rotor speed used was 11 rpm. The individual tablets had a weight of approx. 150 mg. The content of CBD in the FDT tablets was 10 mg, unless otherwise stated. Punch used: 10.00 mm, circular, shallow concave, D tooling.

B: Preparation of Tablet with Two Layers

A layer prepared in the same way as in Example 14A was tableted as the first layer after which the layer of Example 14A (here denoted the second layer) was tableted on top of this first made layer. The ratio of the ingredients was different in this first layer. The weight ratio of the two layers was 70 to 30 (first layer to second layer). Here layer 1 is a lozenge layer and layer 2 is an FDT layer. The individual tablets had a weight of approx. 500 mg with layer 1 being 350 mg and layer 2 being 150 mg. The content of CBD in the tablets was 10 mg in total, unless otherwise stated. Punch used: 10.00 mm, circular, shallow concave, D tooling. Layer 1 is then compressed at a compression force of about 3 kN, after which layer 2 is fused by compression to layer 1 at a compression force of 20 kN. The tablet machine is commissioned by adjusting the fill depth and compression force so the weight and hardness of tablets match the acceptance criteria. A pre-compression force could be included to avoid capping.

Example 15

Composition of Cannabinoid Tablets with Different CBD Source

Cannabinoid tablets based on the procedure in Example 14A were made with the formulations outlined in the examples below. In all of the tablet examples, the amount of the various ingredients is given as % by weight of the tablet.

TABLE 1

It was secured that CBD was thoroughly mixed into the premixture.

| Tablet Number | 100 | 101 | 102 | 103 | 104 |
|---|---|---|---|---|---|
| Raw material name | Content [%] | Content [%] | Content [%] | Content [%] | Content [%] |
| Pre-mixture component | | | | | |
| Mannitol | 30.0 | 30.0 | 30.0 | 30.0 | 30.0 |
| CBD-extract (loaded 50%) | 13.3 | 13.3 | | | |
| CBD isolate (loaded 98.5%)-dissolved in ethanol 1:1 (Example 3) | | | 6.8 | 6.8* | 6.8 |
| FDT components | | | | | |
| Mannitol | 46.9 | 41.9 | 53.4 | 53.4 | 48.4 |
| Flavor | 4.2 | 4.2 | 4.2 | 4.2 | 4.2 |

TABLE 1-continued

It was secured that CBD was thoroughly mixed into the premixture.

| Tablet Number | 100 | 101 | 102 | 103 | 104 |
|---|---|---|---|---|---|
| HIS | 0.1 | 0.1 | 0.1 | 0.1 | 0.1 |
| Processing aids | 0.5 | 0.5 | 0.5 | 0.5 | 0.5 |
| Crospovidone | 5.0 | 10.0 | 5.0 | 5.0 | 10.0 |
| Total | 100 | 100 | 100 | 100 | 100 |

*CBD isolate has been added loosely to the pre-mixture-not dissolved in ethanol-according to the procedure in Example 4 (deviation of the procedure in Example 3).

Example 16

Composition of Cannabinoid Tablets with Different Ratios of Premixture

Cannabinoid tablets based on the procedure in Example 14A were made with the formulations outlined in the examples below. In all of the tablet examples, the amount of the various ingredients is given as % by weight of the tablet.

TABLE 2

It was secured that CBD was thoroughly mixed into the premixture.

| Tablet Number | 105 | 106 | 107 | 108 |
|---|---|---|---|---|
| Raw material name | Content [%] | Content [%] | Content [%] | Content [%] |
| Pre-mixture component | | | | |
| Mannitol | 20.0 | 25.0 | 40.0 | 50.0 |
| CBD-extract (loaded 50%) | 13.3 | 13.3 | 13.3 | 13.3 |
| FDT components | | | | |
| Mannitol | 56.9 | 51.9 | 36.9 | 26.9 |
| Flavor | 4.2 | 4.2 | 4.2 | 4.2 |
| HIS | 0.1 | 0.1 | 0.1 | 0.1 |
| Processing aids | 0.5 | 0.5 | 0.5 | 0.5 |
| Crospovidone | 5.0 | 5.0 | 5.0 | 5.0 |
| Total | 100 | 100 | 100 | 100 |

Example 17

Composition of Cannabinoid Tablets with Different Sugar Alcohol Particles

Cannabinoid tablets based on the procedure in Example 14A were made with the formulations outlined in the examples below. In all of the tablet examples, the amount of the various ingredients is given as % by weight of the tablet.

TABLE 3

It was secured that CBD was thoroughly mixed into the premixture.

| Tablet Number | 109 | 110 | 111 | 112 | 113 |
|---|---|---|---|---|---|
| Raw material name | Content [%] | Content [%] | Content [%] | Content [%] | Content [%] |
| Pre-mixture component | | | | | |
| Isomalt | 30 | | | | |
| Xylitol | | 30 | | | |
| Mannitol | | | 30 | | |
| Maltitol | | | | 30 | |
| Sorbitol | | | | | 30 |
| CBD-extract (loaded 50%) | 13.3 | 13.3 | 13.3 | 13.3 | 13.3 |

TABLE 3-continued

It was secured that CBD was thoroughly mixed into the premixture.

| Tablet Number<br>Raw material name | 109<br>Content [%] | 110<br>Content [%] | 111<br>Content [%] | 112<br>Content [%] | 113<br>Content [%] |
|---|---|---|---|---|---|
| FDT components | | | | | |
| Isomalt | 46.9 | | | | |
| Xylitol | | 46.9 | | | |
| Mannitol | | | 46.9 | | |
| Maltitol | | | | 46.9 | |
| Sorbitol | | | | | 46.9 |
| Flavor | 4.2 | 4.2 | 4.2 | 4.2 | 4.2 |
| HIS | 0.1 | 0.1 | 0.1 | 0.1 | 0.1 |
| Processing aids | 0.5 | 0.5 | 0.5 | 0.5 | 0.5 |
| Crospovidone | 5.0 | 5.0 | 5.0 | 5.0 | 5.0 |
| Total | 100 | 100 | 100 | 100 | 100 |

Example 18

Composition of Cannabinoid Tablets with Different Disintegrants

Cannabinoid tablets based on the procedure in Example 14A were made with the formulations outlined in the examples below. In all of the tablet examples, the amount of the various ingredients is given as % by weight of the tablet.

TABLE 4

It was secured that CBD was thoroughly mixed into the premixture.

| Tablet Number<br>Raw material name | 114<br>Content [%] | 115<br>Content [%] | 116<br>Content [%] | 117<br>Content [%] | 118<br>Content [%] | 119<br>Content [%] |
|---|---|---|---|---|---|---|
| Pre-mixture component | | | | | | |
| Mannitol | 30.0 | 30.0 | 30.0 | 30.0 | 30.0 | 30.0 |
| CBD-extract (loaded 50%) | 13.3 | 13.3 | 13.3 | 13.3 | 13.3 | 13.3 |
| FDT components | | | | | | |
| Mannitol | 46.9 | 46.9 | 46.9 | 26.9 | 26.9 | 26.9 |
| Microcrystalline cellulose (MCC) | | | | 20.0 | 20.0 | 20.0 |
| Flavor | 4.2 | 4.2 | 4.2 | 4.2 | 4.2 | 4.2 |
| HIS | 0.1 | 0.1 | 0.1 | 0.1 | 0.1 | 0.1 |
| Processing aids | 0.5 | 0.5 | 0.5 | 0.5 | 0.5 | 0.5 |
| Crospovidone | 5.0 | | | 5.0 | | |
| Croscarmellose Sodium | | 5.0 | | | 5.0 | |
| Sodium Starch Glycolate | | | 5.0 | | | 5.0 |
| Total | 100 | 100 | 100 | 100 | 100 | 100 |

Example 19

Composition of Cannabinoid Tablets with Microcrystalline Cellulose in Premix

Cannabinoid tablets based on the procedure in Example 14A were made with the formulations outlined in the examples below. In all of the tablet examples, the amount of the various ingredients is given as % by weight of the tablet.

TABLE 5

It was secured that CBD was thoroughly mixed into the premixture.
*CBD isolate has been added loosely to the pre-mixture-not dissolved in ethanol-according to the procedure in Example 4 (deviation of the procedure in Example 3).

| Tablet Number<br>Raw material name | 120<br>Content [%] | 121<br>Content [%] | 122<br>Content [%] | 123<br>Content [%] | 124<br>Content [%] | 125<br>Content [%] |
|---|---|---|---|---|---|---|
| Pre-mixture component | | | | | | |
| Mannitol | 30 | 30 | 30 | 30 | 30 | 30 |
| Microcrystalline cellulose (MCC) | | 3 | 6 | 15 | 6 | 6 |
| CBD-extract (loaded 50%) | 13.3 | 13.3 | 13.3 | 13.3 | | |
| CBD isolate (loaded 98.5%)- dissolved in ethanol 1:1 (Ex 3) | | | | | 6.8* | 6.8 |
| FDT components | | | | | | |
| Mannitol | 46.9 | 43.9 | 40.9 | 31.9 | 47.4 | 47.4 |
| Flavor | 4.2 | 4.2 | 4.2 | 4.2 | 4.2 | 4.2 |
| HIS | 0.1 | 0.1 | 0.1 | 0.1 | 0.1 | 0.1 |
| Processing aids | 0.5 | 0.5 | 0.5 | 0.5 | 0.5 | 0.5 |
| Crospovidone | 5.0 | 5.0 | 5.0 | 5.0 | 5.0 | 5.0 |
| Total | 100 | 100 | 100 | 100 | 100 | 100 |

Example 20

Composition of Cannabinoid Tablets with Different Carriers

Cannabinoid tablets based on the procedure in Example 14A were made with the formulations outlined in the examples below. In all of the tablet examples, the amount of the various ingredients is given as % by weight of the tablet.

TABLE 6

It was secured that CBD was thoroughly mixed into the premixture.
*CBD isolate has been added loosely to the pre-mixture-not dissolved in ethanol-according to the procedure in Example 4 (deviation of the procedure in Example 3). Hyperporous carrier** hyperporous silica magnesium-alumino-metasilicates.

| Tablet Number<br>Raw material name | 126<br>Content [%] | 127<br>Content [%] | 128<br>Content [%] | 129<br>Content [%] | 130<br>Content [%] | 131<br>Content [%] |
|---|---|---|---|---|---|---|
| Pre-mixture component | | | | | | |
| Mannitol | 30 | 30 | 30 | 30 | 30 | 30 |
| Hyperporous carrier** | 3 | 6 | | | 3 | |
| SiO2 | | | 3 | 6 | | 3 |
| CBD-extract (loaded 50%) | 13.3 | 13.3 | 13.3 | 13.3 | | |
| CBD isolate (loaded 98.5%)- dissolved in ethanol 1:1 (Ex 3) | | | | | 6.8* | 6.8* |
| FDT components | | | | | | |
| Mannitol | 43.9 | 40.9 | 43.9 | 40.9 | 50.4 | 50.4 |
| Flavor | 4.2 | 4.2 | 4.2 | 4.2 | 4.2 | 4.2 |
| HIS | 0.1 | 0.1 | 0.1 | 0.1 | 0.1 | 0.1 |

TABLE 6-continued

It was secured that CBD was thoroughly mixed into the premixture.
*CBD isolate has been added loosely to the pre-mixture-not dissolved
in ethanol-according to the procedure in Example 4
(deviation of the procedure in Example 3). Hyperporous carrier**
hyperporous silica magnesium-alumino-metasilicates.

| Tablet Number<br>Raw material<br>name | 126<br>Content<br>[%] | 127<br>Content<br>[%] | 128<br>Content<br>[%] | 129<br>Content<br>[%] | 130<br>Content<br>[%] | 131<br>Content<br>[%] |
|---|---|---|---|---|---|---|
| Processing aids | 0.5 | 0.5 | 0.5 | 0.5 | 0.5 | 0.5 |
| Crospovidone | 5.0 | 5.0 | 5.0 | 5.0 | 5.0 | 5.0 |
| Total | 100 | 100 | 100 | 100 | 100 | 100 |

Example 21

Composition of Cannabinoid Tablets with Different Levels of Disintegrant

Cannabinoid tablets based on the procedure in Example 14A were made with the formulations outlined in the examples below. In all of the tablet examples, the amount of the various ingredients is given as % by weight of the tablet.

TABLE 7

It was secured that CBD was thoroughly mixed into the premixture.
*CBD isolate has been added loosely to the pre-mixture-not
dissolved in ethanol-according to the procedure in Example 4
(deviation of the procedure in Example 3).

| Tablet Number<br>Raw material<br>name | 132<br>Content<br>[%] | 133<br>Content<br>[%] | 134<br>Content<br>[%] | 135<br>Content<br>[%] | 136<br>Content<br>[%] | 137<br>Content<br>[%] |
|---|---|---|---|---|---|---|
| Pre-mixture component | | | | | | |
| Mannitol | 30 | 30 | 30 | 30 | 30 | 30 |
| CBD-extract (loaded 50%) | 13.3 | 13.3 | 13.3 | 13.3 | 13.3 | 13.3 |
| FDT components | | | | | | |
| Mannitol | 49.9 | 47.9 | 45.9 | 43.9 | 41.9 | 36.9 |
| Flavor | 4.2 | 4.2 | 4.2 | 4.2 | 4.2 | 4.2 |
| HIS | 0.1 | 0.1 | 0.1 | 0.1 | 0.1 | 0.1 |
| Processing aids | 0.5 | 0.5 | 0.5 | 0.5 | 0.5 | 0.5 |
| Crospovidone | 2.0 | 4.0 | 6.0 | 8.0 | 10.0 | 15.0 |
| Total | 100 | 100 | 100 | 100 | 100 | 100 |

Example 22

Composition of Cannabinoid Tablets with Different Self-Emulsifying Drug Delivery System (SEDDS) Components Cannabinoid tablets based on the procedure in Example 14A were made with the formulations outlined in the examples below. In all of the tablet examples, the amount of the various ingredients is given as % by weight of the tablet.

TABLE 8

It was secured that CBD was thoroughly mixed into the premixture.

| Tablet Number<br>Raw material<br>name | 138<br>Content<br>[%] | 139<br>Content<br>[%] | 140<br>Content<br>[%] | 141<br>Content<br>[%] | 142<br>Content<br>[%] | 143<br>Content<br>[%] |
|---|---|---|---|---|---|---|
| Pre-mixture component | | | | | | |
| Mannitol | 30.0 | 30.0 | 30.0 | 20.0 | 10.0 | 10.0 |
| CBD-extract (loaded 50%) | | | | 13.3 | 13.3 | |
| CBD isolate (loaded 98.5%) | 6.8 | 6.8 | 6.8 | | | |
| Labrafil M 1944 CS | 6.8 | | | | | |
| Gelucire 50/13 | | | 6.8 | | | |
| Labrasol ALF | | 3.3 | | 13.3 | | |
| Maisine CC | 13.3 | | | | | |
| Labrafac Lipophile WL 1349 | | 8.0 | | | | |
| Propylene Glycol | | 2.0 | | 13.3 | | |
| Soluplus | | | | | 40.0 | |
| CBD-cyclodextrin | | | | | | 40.0 |
| FDT components | | | | | | |
| Mannitol | 33.3 | 30.1 | 46.6 | 30.3 | 26.9 | 40.2 |
| Flavors | 4.2 | 4.2 | 4.2 | 4.2 | 4.2 | 4.2 |
| HIS | 0.1 | 0.1 | 0.1 | 0.1 | 0.1 | 0.1 |
| Processing aids | 0.5 | 0.5 | 0.5 | 0.5 | 0.5 | 0.5 |
| Crospovidone | 5.0 | 5.0 | 5.0 | 5.0 | 5.0 | 5.0 |
| Total | 100 | 100 | 100 | 100 | 100 | 100 |

Example 23

Preparation of Fast Disintegrating Tablet

Cannabinoid tablets based on the procedure in Example 14A were made with the formulations outlined in the examples below. In these example, the following conditions where applied. Punch used: 7.00 mm, circular, shallow concave, B tooling. Tablet weight: 100.0 mg. In these examples, the amount of the various ingredients is given as mg.

TABLE 9

Fast disintegrating tablet compositions with CBD isolate.
Amounts are given in mg. FDT = Fast disintegrating tablet.

| | FDT(a) | FDT(b) | FDT(c) | FDT(d) | FDT(e) | FDT(f) |
|---|---|---|---|---|---|---|
| CBD | 10.0 | 10.0 | 10.0 | 10.0 | 10.0 | 10.0 |
| Microcrystalline cellulose | — | — | — | 39.6 | 39.6 | 39.6 |
| Mannitol | 79.2 | 79.2 | 79.2 | 39.6 | 39.6 | 39.6 |
| Crospovidone | 5.0 | — | — | 5.0 | — | — |
| Croscarmellose Sodium | — | 5.0 | — | — | 5.0 | — |
| Sodium Starch Glycolate | — | — | 5.0 | — | — | 5.0 |
| Peppermint | 4.0 | 4.0 | 4.0 | 4.0 | 4.0 | 4.0 |
| Menthol | 0.4 | 0.4 | 0.4 | 0.4 | 0.4 | 0.4 |
| Sucralose | 0.4 | 0.4 | 0.4 | 0.4 | 0.4 | 0.4 |
| Silicium dioxide | — | — | — | 1.0 | 1.0 | 1.0 |
| Magnesium stearate | 1.0 | 1.0 | 1.0 | 1.0 | 1.0 | 1.0 |
| Total | 100.0 | 100.0 | 100.0 | 100.0 | 100.0 | 100.0 |

Example 24

Composition of Cannabinoid Tablets with Ready to Use Disintegrants

Cannabinoid tablets based on the procedure in Example 14A were made with the formulations outlined in the examples below. In these example, the following conditions where applied. Punch used: 7.00 mm, circular, shallow concave, B tooling. Tablet weight: 100.0 mg. In these examples, the amount of the various ingredients is given as mg.

Another way of preparing fast disintegrating tablets would be to use a ready to use system. In the present example five fast disintegrating tablets (FDT(g)-FDT(k)) without cannabinoids are prepared with ready to use systems in formulations as outlined in Table 10.

TABLE 10

Fast disintegrating tablet compositions with different ready to use systems. Amounts are given in mg. FDT = Fast disintegrating tablet.

|  | FDT(g) | FDT(h) | FDT(i) | FDT(j) | FDT(k) |
|---|---|---|---|---|---|
| Ludiflash | 86.7 | — | — | — | — |
| Pearlitol Flash | — | 86.7 | — | — | — |
| SmartEx QD50 | — | — | 86.7 | — | — |
| F-Melt | — | — | — | 88.7 | — |
| ProSolv ODT G2 | — | — | — | — | 88.7 |
| Peppermint | 4.4 | 4.4 | 4.4 | 4.4 | 4.4 |
| Menthol | 1.5 | 1.5 | 1.5 | 1.5 | 1.5 |
| Sucralose | 0.4 | 0.4 | 0.4 | 0.4 | 0.4 |
| Crospovidone | 5.0 | 5.0 | 5.0 | — | — |
| Croscarmellose Sodium | — | — | — | 3.0 | — |
| Sodium Starch Glycolate | — | — | — | — | 3.0 |
| Magnesium stearate | 2.0 | 2.0 | 2.0 | 2.0 | 2.0 |
| Total | 100.0 | 100.0 | 100.0 | 100.0 | 100.0 |

Additionally, five fast disintegrating tablets (FDT(l)-FDT(p)) with cannabinoids are prepared with ready to use systems in formulations as outlined in Table 11.

TABLE 11

Fast disintegrating tablet compositions with different ready to use systems and CBD isolate. Amounts are given in mg. FDT = Fast disintegrating tablet.

|  | FDT(l) | FDT(m) | FDT(n) | FDT(o) | FDT(p) |
|---|---|---|---|---|---|
| CBD | 10.0 | 10.0 | 10.0 | 10.0 | 10.0 |
| Ludiflash | 76.7 | — | — | — | — |
| Pearlitol Flash | — | 76.7 | — | — | — |
| SmartEx QD50 | — | — | 76.7 | — | — |
| F-Melt | — | — | — | 76.7 | — |
| ProSolv ODT G2 | — | — | — | — | 76.7 |
| Peppermint | 4.4 | 4.4 | 4.4 | 4.4 | 4.4 |
| Menthol | 1.5 | 1.5 | 1.5 | 1.5 | 1.5 |
| Sucralose | 0.4 | 0.4 | 0.4 | 0.4 | 0.4 |
| Crospovidone | 5.0 | 5.0 | 5.0 | — | — |
| Croscarmellose Sodium | — | — | — | 3.0 | — |
| Sodium Starch Glycolate | — | — | — | — | 3.0 |
| Magnesium stearate | 2.0 | 2.0 | 2.0 | 2.0 | 2.0 |
| Total | 100.0 | 100.0 | 100.0 | 100.0 | 100.0 |

Further four fast disintegrating tablets (FDT(1)-FDT(4)) with cannabinoids are prepared with varying amounts of MCC (microcrystalline cellulose) as filler, as outlined in Table 12.

TABLE 12

Fast disintegrating tablet compositions with varying amounts of MCC and CBD as isolate. Amounts are given in mg. FDT = Fast disintegrating tablet.

|  | FDT(1) | FDT(2) | FDT(3) | FDT(4) |
|---|---|---|---|---|
| CBD | 10.0 | 10.0 | 10.0 | 10.0 |
| Microcrystalline cellulose (MCC) | 0.0 | 5.0 | 10.0 | 20.0 |
| Mannitol | 77.7 | 72.7 | 67.7 | 57.7 |
| Crospovidone | 5.0 | 5.0 | 5.0 | 5.0 |
| Peppermint | 4.4 | 4.4 | 4.4 | 4.4 |
| Menthol | 1.5 | 1.5 | 1.5 | 1.5 |
| Sucralose | 0.4 | 0.4 | 0.4 | 0.4 |
| Magnesium stearate | 1.0 | 1.0 | 1.0 | 1.0 |
| Total | 100.0 | 100.0 | 100.0 | 100.0 |

Four fast disintegrating tablets, FDT(5)-FDT(8), with cannabinoids are prepared with varying amounts of disintegrant, as outlined in Table 13.

TABLE 13

Fast disintegrating tablet compositions with varying amount of disintegrant and CBD isolate. Amounts are given in mg. FDT = Fast disintegrating tablet.

|  | FDT(5) | FDT(6) | FDT(7) | FDT(8) |
|---|---|---|---|---|
| CBD | 10.0 | 10.0 | 10.0 | 10.0 |
| Mannitol | 39.7 | 37.2 | 39.7 | 29.7 |
| Microcrystalline cellulose (MCC) | 43 | 43 | 43 | 43 |
| Crospovidone | 0.0 | 2.5 | 5.0 | 10.0 |
| Peppermint | 4.4 | 4.4 | 4.4 | 4.4 |
| Menthol | 1.5 | 1.5 | 1.5 | 1.5 |
| Sucralose | 0.4 | 0.4 | 0.4 | 0.4 |
| Magnesium stearate | 1.0 | 1.0 | 1.0 | 1.0 |
| Total | 100.0 | 100.0 | 100.0 | 100.0 |

Three fast disintegrating tablets, FDT(9)-FDT(11), with cannabinoids are prepared with varying types of lubricants, as outlined in Table 14.

TABLE 14

Fast disintegrating tablet compositions with different types of lubricants and CBD isolate. Amounts are given in mg. FDT = Fast disintegrating tablet.

|  | FDT(9) | FDT(10) | FDT(11) |
|---|---|---|---|
| CBD | 10.0 | 10.0 | 10.0 |
| Microcrystalline cellulose (MCC) | 5.0 | 5.0 | 5.0 |
| Mannitol | 76.6 | 75.6 | 75.6 |
| Crospovidone | 5.0 | 5.0 | 5.0 |
| Eucamenthol Flavour | 2.0 | 2.0 | 2.0 |
| Sucralose | 0.4 | 0.4 | 0.4 |
| Magnesium stearate | 1.0 | — | — |
| Sodium stearyl fumarate | — | 2.0 | — |
| Compritol HD5 | — | — | 2.0 |
| Total | 100.0 | 100.0 | 100.0 |

Three fast disintegrating tablets, FDT(12)-FDT(14), with cannabinoids are prepared, as outlined in Table 15.

In this example, the following conditions where applied. Punch used: 7.00 mm, circular, shallow concave, B tooling. Tablet weight: 75.0 mg.

TABLE 15

Fast disintegrating tablet compositions with CBD isolate.
Amounts are given in mg. FDT = Fast disintegrating tablet.
FDT(13) was made similar to FDT(12) but without buffer.
FDT(14) was made similar to FDT(12) but without disintegrant.

|  | FDT(12) | FDT(13) | FDT(14) |
|---|---|---|---|
| SmartEx QD 50 | 53.0 | 58.0 | 58.0 |
| CBD | 10.0 | 10.0 | 10.0 |
| Sodium carbonate anhydrous | 5.0 | 0.0 | 5.0 |
| Crospovidone | 5.0 | 5.0 | 0.0 |
| Peppermint Powder | 0.4 | 0.4 | 0.4 |
| Sucralose | 0.4 | 0.4 | 0.4 |
| Silicium dioxide (Aerosil 200) | 0.2 | 0.2 | 0.2 |
| Magnesium Stearate | 1.0 | 1.0 | 1.0 |
| Total | 75.0 | 75.0 | 75.0 |

FDT(12)-FDT(13) were pressed to a hardness of 15-20 N. FDT (14) was pressed to a hardness of 25-35 N.

Example 25

Disintegration of Tablets

The in vitro disintegration of the fast disintegrating tablets of Examples 15-24 was carried out in accordance to European Pharmacopeia 9.0, section 2.9.1, *Disintegration of tablets and capsules*. The results for Example 23 are outlined in Table 16. A minimum and a maximum value for measured disintegration are given and this is more or less a function of the hardness.

TABLE 16

In vitro disintegration, hardness, friability. Time is given in seconds.

|  | Mean in vitro disintegration (sec) | | Mean hardness (N) | | Mean friability (%) | |
|---|---|---|---|---|---|---|
|  | Min (sec) | Max (sec) | Min (N) | Max (N) | Min (%) | Max (%) |
| FDT(a) | 21 | 24 | 14 | 63 | 0.0 | 0.3 |
| FDT(b) | 23 | 98 | 12 | 50 | 0.0 | 0.6 |
| FDT(c) | 29 | 177 | 14 | 55 | 0.0 | 0.5 |
| FDT(d) | 15 | 177 | 19 | 62 | 0.0 | 0.0 |
| FDT(e) | 13 | 175 | 15 | 45 | 0.0 | 0.2 |
| FDT(f) | 11 | 259 | 14 | 43 | 0.0 | 0.2 |

The above table should be interpreted as illustrated in the following example. When looking at e.g. FDT(a), the minimum mean disintegration time of 21 seconds correspond to a tablet pressed just hard enough to obtain a cohesive tablet having a minimum mean hardness of 14 N and a friability of 0.3%. Similarly, the maximum mean disintegration time of 24 seconds correspond to another tablet pressed harder to have a maximum mean hardness of 63 N. In this way, the tablet having a mean friability of 0.0% of FDT(a) corresponds to the tablet having a mean hardness of 63 N. In other words, in table 4 FDT(a) refers to two different tablets pressed at two different pressures, the linking being indicated above. I.e. each line corresponds to two different tablets, one for Min values of disintegration time and hardness and the Max value for friability, and another for Max values of disintegration time and hardness and the Min value for friability.

The results for Example 24 are outlined in Table 17.

TABLE 17

In vitro disintegration, hardness, friability. Time is given in seconds.

|  | Mean in vitro disintegration (sec) | | Mean hardness (N) | | Mean friability (%) | |
|---|---|---|---|---|---|---|
|  | Min (sec) | Max (sec) | Min (N) | Max (N) | Min (%) | Max (%) |
| FDT(g) | 120 | 210 | 17 | 22 | N/A | 0.5 |
| FDT(h) | 40 | 80 | 16 | 24 | 0.5 | 0.8 |
| FDT(i) | 10 | 46 | 17 | 22 | 0.3 | 0.3 |
| FDT(j) | 42 | 150 | 17 | 22 | 0.7 | 1.0 |
| FDT(k) | 45 | 201 | 17 | 22 | 0.6 | 0.9 |

The above table should be interpreted as illustrated in the example below Table 16.

It is seen that the in vitro disintegrating may vary a lot between the disclosed fast disintegrating tablets.

In vitro tests were also repeated for some of the ready to use systems in FDT(l)-FDT(p).

The in vitro disintegration is a fast method to determine the time and mechanism for tablet performance. More preferable or in combination the in vivo disintegration is measured. The in vivo disintegration time is a value for the actual disintegration of the tablet under the tongue. Table 18 and 19 highlights the results for in vivo disintegration.

TABLE 18

In vivo disintegration. Time is given in seconds.

|  | Mean in vivo disintegration (sec) | |
|---|---|---|
|  | Min (sec) | Max (sec) |
| FDT(a) | 34 | 52 |
| FDT(b) | 18 | 27 |
| FDT(c) | 37 | N/A |
| FDT(d) | 42 | N/A |
| FDT(e) | 46 | N/A |

TABLE 19

In vivo disintegration. Time is given in seconds.

|  | Mean in vivo disintegration (sec) | |
|---|---|---|
|  | Min (sec) | Max (sec) |
| FDT(g) | 19 | 40 |
| FDT(h) | 13 | 48 |
| FDT(i) | 32 | 80 |
| FDT(j) | N/A | 56 |
| FDT(k) | N/A | 81 |

The above Tables 18 and 19 should be interpreted as illustrated in the example below Table 16.

In vivo tests were also repeated for some of the ready to use systems in FDT(l)-FDT(p).

As recognized for the in vitro disintegration results above the speed of in vivo disintegrating may be varied between the disclosed batches. The disintegration time should be complete within 60 seconds from the onset of disintegration or preferable faster.

Example 26

Composition of Cannabinoid Tablets with Two Layers

Cannabinoid tablets based on the procedure in Example 14B were made with the formulations outlined in the examples below. In all of the tablet examples, the amount of the various ingredients is given as % by weight of the tablet layer.

TABLE 20

It was secured that CBD was thoroughly mixed into the premixture.

| Raw material name | Content [%] Layer 1-350 mg | Content [%] Layer 2-150 mg |
|---|---|---|
| Pre-mixture component | | |
| Mannitol | 50.0 | 40.0 |
| CBD-extract (loaded 50%) | 4.0 | 4.0 |
| FDT components | | |
| Mannitol | 40.7 | 49.2 |
| Flavor | 4.2 | 4.2 |
| HIS | 0.1 | 0.1 |
| Processing aids | 1.0 | 1.0 |
| Crospovidone | | 1.5 |
| Total | 100 | 100 |

Example 27

Composition of Cannabinoid Two-Layered Tablets with Different Levels of CBD

Cannabinoid tablets based on the procedure in Example 14B were made with the formulations outlined in the examples below. In all of the tablet examples, the amount of the various ingredients is given as % by weight of the tablet layer.

TABLE 21

Compositions of first and second layers.

| Tablet no. | 1 | 2 | 3 | 4 | 5 | 6 | 7 | 8 |
|---|---|---|---|---|---|---|---|---|
| Raw material layer 1 | Content in weight percent of Layer 1 | | | | | | | |
| Mannitol | 98.25 | 98.25 | 98.25 | 98.25 | 98.25 | 98.25 | 98.25 | 98.25 |
| Flavor | 1 | 1 | 1 | 1 | 1 | 1 | 1 | 1 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material layer 2 | Content in weight percent of Layer 2 | | | | | | | |
| Mannitol | 84.25 | 80.25 | 76.95 | 75.25 | 70.25 | 65.25 | 60.25 | 55.25 |
| Disintegrant | 8 | 8 | 8 | 8 | 8 | 8 | 8 | 8 |
| Flavor | 1 | 1 | 1 | 1 | 1 | 1 | 1 | 1 |
| HIS | 0.25 | 0.25 | 0.25 | 0.25 | 0.25 | 0.25 | 0.25 | 0.25 |
| CBD-extract (loaded 50%) | 6.0 | 10.0 | 13.3 | 15.0 | 20.0 | 25.0 | 30.0 | 35.0 |
| MgSt | 0.5 | 0.5 | 0.5 | 0.5 | 0.5 | 0.5 | 0.5 | 0.5 |
| Total layer 2 | 100 | 100 | 100 | 100 | 100 | 100 | 100 | 100 |

Example 28

Composition of Cannabinoid Two-Layered Tablets with Different Level of Super Disintegrant Cannabinoid tablets based on the procedure in Example 14B were made with the formulations outlined in the examples below. In all of the tablet examples, the amount of the various ingredients is given as % by weight of the tablet layer.

TABLE 22

Compositions of first and second layers. Super disintegrant is Crospovidone.

| Tablet no. | 9 | 10 | 11 | 12 | 13 | 14 | 15 | 16 |
|---|---|---|---|---|---|---|---|---|
| Raw material | \multicolumn{8}{c}{Content in weight percent of Layer 1} | | | | | | | |
| Mannitol | 98.25 | 98.25 | 98.25 | 98.25 | 98.25 | 98.25 | 98.25 | 98.25 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material | \multicolumn{8}{c}{Content in weight percent of Layer 2} | | | | | | | |
| Mannitol | 83.95 | 82.95 | 80.95 | 78.95 | 76.95 | 74.95 | 72.95 | 70.95 |
| Super disintegrant | 1 | 2 | 4 | 6 | 8 | 10 | 12 | 14 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| CBD-extract (loaded 50%) | 13.3 | 13.3 | 13.3 | 13.3 | 13.3 | 13.3 | 13.3 | 13.3 |
| MgSt | 0.5 | 0.5 | 0.5 | 0.5 | 0.5 | 0.5 | 0.5 | 0.5 |
| Total layer 2 | 100 | 100 | 100 | 100 | 100 | 100 | 100 | 100 |

Example 29

Composition of Cannabinoid Two-Layered Tablets with Ready to Use Disintegrant

Cannabinoid tablets based on the procedure in Example 14B were made with the formulations outlined in the examples below. In all of the tablet examples, the amount of the various ingredients is given as % by weight of the tablet layer.

TABLE 23

Compositions of first and second layers. Content of starch disintegrant is based on the content of starch in Pearlitol Flash.

| Tablet no. | 17 | 18 | 19 | 20 | 21 | 22 | 23 | 24 |
|---|---|---|---|---|---|---|---|---|
| Raw material | \multicolumn{8}{c}{Content in weight percent of Layer 1} | | | | | | | |
| Mannitol | 98.25 | 98.25 | 98.25 | 98.25 | 98.25 | 98.25 | 98.25 | 98.25 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material | \multicolumn{8}{c}{Content in weight percent of Layer 2} | | | | | | | |
| Content of starch disintegrant | 2 | 4 | 6 | 8 | 10 | 12 | 14 | 16 |
| Mannitol | 72.15 | 60.45 | 48.65 | 36.85 | 25.15 | 13.35 | 6.55 | 4.85 |
| Pearlitol Flash | 11.8 | 23.5 | 35.3 | 47.1 | 58.8 | 70.6 | 77.4 | 80.1 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| CBD-extract (loaded 50%) | 13.3 | 13.3 | 13.3 | 13.3 | 13.3 | 13.3 | 13.3 | 13.3 |
| MgSt | 0.5 | 0.5 | 0.5 | 0.5 | 0.5 | 0.5 | 0.5 | 0.5 |
| Total layer 2 | 100 | 100 | 100 | 100 | 100 | 100 | 100 | 100 |

Example 30

Composition of Cannabinoid Two-Layered Tablets with CBD in Both Layers

Cannabinoid tablets based on the procedure in Example 14B were made with the formulations outlined in the examples below. In all of the tablet examples, the amount of the various ingredients is given as % by weight of the tablet layer.

TABLE 24

Compositions of first and second layers.

| Tablet no. | 25 | 26 | 27 | 28 | 29 | 30 | 31 | 32 |
|---|---|---|---|---|---|---|---|---|
| Raw material | Content in weight percent of Layer 1 | | | | | | | |
| Mannitol | 95.25 | 92.55 | 86.85 | 75.45 | 98.25 | 98.25 | 98.25 | 98.25 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| CBD-extract (loaded 50%) | 3.0 | 5.7 | 11.4 | 22.8 | — | — | — | — |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material | Content in weight percent of Layer 2 | | | | | | | |
| Mannitol | 76.95 | 76.95 | 76.95 | 76.95 | 76.95 | 76.95 | 76.95 | 76.95 |
| Super disintegrant | 8 | 8 | 8 | 8 | 8 | 8 | 8 | 8 |
| Flavor | 1 | 1 | 1 | 1 | 1 | 1 | 1 | 1 |
| HIS | 0.25 | 0.25 | 0.25 | 0.25 | 0.25 | 0.25 | 0.25 | 0.25 |
| CBD-extract (loaded 50%) | 13.3 | 13.3 | 13.3 | 13.3 | 13.3 | 13.3 | 13.3 | 13.3 |
| MgSt | 0.5 | 0.5 | 0.5 | 0.5 | 0.5 | 0.5 | 0.5 | 0.5 |
| Total layer 2 | 100 | 100 | 100 | 100 | 100 | 100 | 100 | 100 |

Example 31A

Composition of Cannabinoid Two-Layered Tablets with Different Sugar Alcohols

Cannabinoid tablets based on the procedure in Example 14B were made with the formulations outlined in the examples below. In all of the tablet examples, the amount of the various ingredients is given as % by weight of the tablet layer.

TABLE 26

Compositions of first and second layers.

| Tablet no. | 33 | 34 | 35 | 36 | 37 | 38 | 39 | 40 |
|---|---|---|---|---|---|---|---|---|
| Raw material | Content in weight percent of Layer 1 | | | | | | | |
| Mannitol | 97.75 | — | — | — | 50.00 | 50.00 | 50.00 | — |
| Isomalt | — | 97.75 | — | — | 47.75 | — | — | 50.00 |
| Sorbitol | — | — | 97.75 | — | — | 47.75 | — | 47.75 |
| Maltitol | — | — | — | 97.75 | — | — | 47.75 | — |
| Buffer | 0.5 | 0.5 | 0.5 | 0.5 | 0.5 | 0.5 | 0.5 | 0.5 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material | Content in weight percent of Layer 2 | | | | | | | |
| Mannitol | 76.95 | 67.15 | 56.95 | 46.95 | 37.05 | 26.95 | — | 46.95 |
| Erythritol | — | 10 | 20 | 30 | 40 | 50 | 76.95 | — |
| Xylitol | — | — | — | — | — | — | — | 30 |
| Disintegrant | 8 | 8 | 8 | 8 | 8 | 8 | 8 | 8 |
| Flavor | 1 | 1 | 1 | 1 | 1 | 1 | 1 | 1 |
| HIS | 0.25 | 0.25 | 0.25 | 0.25 | 0.25 | 0.25 | 0.25 | 0.25 |
| CBD-extract (loaded 50%) | 13.3 | 13.3 | 13.3 | 13.3 | 13.3 | 13.3 | 13.3 | 13.3 |
| MgSt | 0.5 | 0.5 | 0.5 | 0.5 | 0.5 | 0.5 | 0.5 | 0.5 |
| Total layer 2 | 100 | 100 | 100 | 100 | 100 | 100 | 100 | 100 |

Example 31B

Composition of Cannabinoid Two-Layered Tablets with Different Sugar Alcohols

Cannabinoid tablets based on the procedure in Example 14B were made with the formulations outlined in the examples below. In all of the tablet examples, the amount of the various ingredients is given as % by weight of the tablet layer. Tablet no. 41-42 are 400 mg tablets each made with 300 mg first layer and 100 mg second layer. Tablet no. 43-48 are 500 mg tablets each made with 350 mg first layer and 150 mg second layer.

TABLE 26

Compositions of first and second layers.

| Tablet no. | 41 | 42 | 43 | 44 | 45 | 46 | 47 | 48 |
|---|---|---|---|---|---|---|---|---|
| Raw material | \multicolumn{8}{c}{Content in weight percent of Layer 1} | | | | | | | |
| Mannitol | 93.3 | — | — | — | — | — | — | — |
| Isomalt | — | 93.3 | 98.20 | 98.20 | 98.20 | 98.20 | — | 96.06 |
| Sorbitol | — | — | — | — | — | — | 98.20 | 0 |
| HIS | 1.7 | 1.7 | 0.25 | 0.25 | 0.25 | 0.25 | 0.25 | 0.25 |
| Flavor | 4.0 | 4.0 | 1.05 | 1.05 | 1.05 | 1.05 | 1.05 | 1.05 |
| Xanthan gum | — | — | — | — | — | — | — | 2.14 |
| MgSt | 1.0 | 1.0 | 0.5 | 0.5 | 0.5 | 0.5 | 0.5 | 0.5 |
| Total layer 1 | 100 | 100 | 100 | 100 | 100 | 100 | 100 | 100 |
| Raw material | \multicolumn{8}{c}{Content in weight percent of Layer 2} | | | | | | | |
| Mannitol | 64.70 | 64.70 | 84.95 | 36.12 | — | 35.78 | 84.95 | 84.95 |
| Erythritol | — | — | — | — | — | 49.07 | — | — |
| Pearlitol Flash | — | — | — | 48.83 | 84.95 | — | — | — |
| Microcrystalline cellulose (MCC) | 5.00 | 5.00 | — | — | — | — | — | — |
| Super disintegrant | 10.00 | 10.00 | — | — | — | — | — | — |
| Buffer | 5.00 | 5.00 | — | — | — | — | — | — |
| HIS | — | — | 0.25 | 0.25 | 0.25 | 0.25 | 0.25 | 0.25 |
| Flavor | — | — | 1.00 | 1.00 | 1.00 | 1.00 | 1.00 | 1.00 |
| MgSt | — | — | 0.50 | 0.50 | 0.50 | 0.60 | 0.50 | 0.50 |
| Sodium Stearyl Fumerate | 2.00 | 2.00 | — | — | — | — | — | — |
| CBD-extract (loaded 50%) | 13.3 | 13.3 | 13.3 | 13.3 | 13.3 | 13.3 | 13.3 | 13.3 |
| Total layer 2 | 100 | 100 | 100 | 100 | 100 | 100 | 100 | 100 |

Example 31C

Composition of Cannabinoid Two-Layered Tablets with Different Cannabinoid Sources Cannabinoid tablets based on the procedure in Example 14B were made with the formulations outlined in the examples below. In all of the tablet examples, the amount of the various ingredients is given as % by weight of the tablet.

TABLE 27

Compositions of first and second layers.
*CBD sorbed onto carrier in a weight ratio of 1:2

| Tablet no. | 49 | 50 | 51 | 52 | 53 | 54 | 55 | 56 |
|---|---|---|---|---|---|---|---|---|
| Raw material layer 1 | \multicolumn{8}{c}{Content in weight percent of Layer 1} | | | | | | | |
| Mannitol | 97.75 | 97.75 | 97.75 | 97.75 | 97.75 | 97.75 | 97.75 | 97.75 |
| Buffer | 0.5 | 0.5 | 0.5 | 0.5 | 0.5 | 0.5 | 0.5 | 0.5 |
| Flavor | 1 | 1 | 1 | 1 | 1 | 1 | 1 | 1 |

TABLE 27-continued

Compositions of first and second layers.
*CBD sorbed onto carrier in a weight ratio of 1:2

| Tablet no. | 49 | 50 | 51 | 52 | 53 | 54 | 55 | 56 |
|---|---|---|---|---|---|---|---|---|
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total layer 1 | 100 | 100 | 100 | 100 | 100 | 100 | 100 | 100 |
| Raw material layer 2 | | | Content in weight percent of Layer 2 | | | | | |
| CBD isolate (loaded 98.5%)-dissolved in ethanol 1:1 (Example 3)-MCC* | 20.4 | — | — | — | — | — | — | — |
| CBD-extract (loaded 50%)-MCC* | — | 39.9 | — | — | — | — | — | — |
| CBD isolate (loaded 98.5%)-dissolved in ethanol 1:1 (Example 3)-sugar alcohol | — | — | 20.4 | — | — | — | — | — |
| CBD-extract (loaded 50%)-sugar alcohol* | — | — | — | 39.9 | — | — | — | — |
| CBD-extract (loaded 50%) | — | — | — | — | 13.3 | 13.3 | 13.3 | 13.3 |
| Mannitol | 62.3 | 42.8 | 62.3 | 42.8 | — | — | — | — |
| Ludiflash | — | — | — | — | 74.4 | — | — | — |
| SmartEx QD50 | — | — | — | — | — | 74.4 | — | — |
| F-Melt | — | — | — | — | — | — | 74.4 | — |
| ProSolv ODT G2 | — | — | — | — | — | — | — | 74.4 |
| Crospovidone | 5.0 | 5.0 | 5.0 | 5.0 | — | — | — | — |
| Flavor | 5.9 | 5.9 | 5.9 | 5.9 | 5.9 | 5.9 | 5.9 | 5.9 |
| HIS | 0.4 | 0.4 | 0.4 | 0.4 | 0.4 | 0.4 | 0.4 | 0.4 |
| Buffer | 5.0 | 5.0 | 5.0 | 5.0 | 5.0 | 5.0 | 5.0 | 5.0 |
| MgSt | 1.0 | 1.0 | 1.0 | 1.0 | 1.0 | 1.0 | 1.0 | 1.0 |
| Total | 100.0 | 100.0 | 100.0 | 100.0 | 100.0 | 100.0 | 100.0 | 100.0 |

Example 32

Evaluations of Two-Layered Tablets—First Layer of Tablet No. 43, 47 and 48

Tablet no. 43, 47 and 48 were each manufactured in three versions, where the applied pressure used to press the first layer was 10 kN, 20 kN, and 30 kN (single punch device with a punch diameter of 10.0 mm), respectively. Five tablets were made for each of these versions. For each version of the tablets 43, 47 and 48, a breaking point test, a fragility test and a dissolution time measurement were performed on the first layer. For measuring breaking point, a PTB 311 from Pharma Test was used.

The fragility test involved evaluating the number of crushed layers produced. When all five were intact, a "pass" grade was assigned, whereas one or more crushed layers is indicated by the number of crushed layers. Alternatively, friability could be used as a measure of the fragility.

To test dissolution time, the following method was used. 15 mL of 0.02 M potassium dihydrogen phosphate-buffer (pH adjusted to 7.4) is added to 50 mL of water in a measuring tube with a screw cap. The tablet is inserted in the measuring tube and the screw cap is fastened. The measuring tube is fixated horizontally. The measuring tube is vibrated at about 110 RPM such that the tablet can move back and forth in the measuring tube. The measuring tube is vibrated until the tablet or module thereof in question is completely dissolved and the time of vibration is noted as the dissolution time.

TABLE 28

Fragility test indicates number of tablets crushed during testing, or "pass" when no tablets were crushed.

| Test | Compression force [kN] | Tablet no. 43 Layer 1 (lozenge layer) | Tablet no. 47 Layer 1 (lozenge layer) | Tablet no. 48 Layer 1 (lozenge layer) |
|---|---|---|---|---|
| Breaking point | 10 | 193 N | 237 N | 195 N |
|  | 20 | 232 N | 239 N | 229 N |
|  | 30 | 205 N | 249 N | 220 N |
| Fragility | 10 | Pass | Pass | Pass |
|  | 20 | Pass | Pass | Pass |
|  | 30 | Pass | Pass | Pass |
| Dissolution time | 10 | 9 min, 7 sec | 6 min, 12 sec | 12 min 10 sec |
|  | 20 | 9 min, 41 sec | 6 min, 38 sec | 13 min 32 sec |
|  | 30 | 9 min, 50 sec | 7 min, 05 sec | 16 min 0 sec |

As can be seen from Table 28, the breaking points test reveals that Tablet no. 47 having a first layer based on sorbitol as the sugar alcohol gives a higher breaking point that Tablet no. 43 having a first layer based on isomalt as the sugar alcohol. Tablet no. 43 showed that the version pressed with 30 kN actually had a lower breaking point than that pressed with 20 kN, indicating that 30 kN pressing force would be too high and that the direct compressibility of the sugar alcohol (isomalt) is compromised.

Also, it is observed that all tested layers scored a pass in the fragility test, meaning that none of the five of each version was evaluated to be fragile or crushed during manufacturing.

Further, dissolution time test showed that sorbitol-based Tablet no. 47 generally dissolved faster than isomalt-based Tablet no. 43. Further, a higher pressing forces resulted in longer dissolution time.

Finally, Tablet no. 48 is compared with Tablet no. 43. Tablet no. 48 is somewhat similar to Tablet no. 43, but additionally comprising xanthan gum. As seen from Table 28, addition of xanthan gum did not noticeably affect breaking point test or fragility test, however, the dissolution time was significantly increased from around 9-10 minutes for Tablet no. 43 to about 12-16 minutes for Tablet no. 48, demonstrating effect of xanthan gum to delay dissolution and hence release of its constituents, such as sugar alcohol, flavor, nicotine (if any) etc. While obtaining the above, no compromising of the masking effect of the first layer was observed.

Example 33

Evaluations of Two-Layered Tablets—Second Layer of Tablet No. 43-46

Tablet no. 43-46 were each manufactured in three versions, where the applied pressure used to press the first layer was 10 kN, 20 kN, and 30 kN, respectively. Five tablets were made for each of these versions. For each version of the tablets 43-46 a breaking point test, a fragility test and a dissolution time measurement were performed on the second layer.

TABLE 29

Fragility test indicates number of tablets crushed during testing, or "pass" when no tablets were crushed.

| Test | Compr. force [kN] | Tablet no. 43 Layer 2 (FDT layer) | Tablet no. 44 Layer 2 (FDT layer) | Tablet no. 45 Layer 2 (FDT layer) | Tablet no. 46 Layer 2 (FDT layer) |
| --- | --- | --- | --- | --- | --- |
| Breaking point | 10 | 50 N | 46 N | 43 N | 13 N |
| | 20 | N/A | 55 N | 62 N | 20 N |
| | 30 | N/A | 72 N | 73 N | 11 N |
| Fragility | 10 | 1 tablet | 1 tablet | 1 tablet | 5 tablets |
| | 20 | N/A | Pass | Pass | 5 tablets |
| | 30 | N/A | Pass | Pass | 5 tablets |
| Dissolution time | 10 | 2 min, 20 sec | 50 sec | 50 sec | 35 sec |
| | 20 | N/A | 1 min, 15 sec | 50 sec | 1 min 40 sec |
| | 30 | N/A | 2 min, 08 sec | 1 min 17 sec | 2 min 50 sec |

First, looking at Tablet no. 43-45, Table 29 shows that the breaking point of the second layers of the produced tablets generally increases with increasing compressing force from 10 kN to 30 kN.

Nevertheless, the table also shows that fragility may be a concern. It is noted that Tablet no. 43 performed reasonably well with only 1 tablet breaking during testing.

Table 29 also shows that a trade-off may exist between applying a sufficient compression force to obtain a non-fragile second layer, but that increasing the compression force also impacts the dissolution time.

Further, it is noted that using disintegrant in the second layer (Tablet no. 44-45) resulted in decreased dissolution time over no disintegrant in the second layer (Tablet no. 43), and further that increasing the amount of disintegrant as in Tablet no. 45 over Tablet no. 44 lead to a further decrease in dissolution time.

Taking also Tablet no. 46 into account, it is noted that while very fragile second modules were produced, a rather short dissolution time was measured. It is noted that when evaluating the particle size distribution of the mannitol used in Tablet no. 43-44 and 46, the Pearlitol Flash used in Tablet no. 44-45, and the erythritol used in Tablet no. 46, the Pearlitol Flash showed the smallest particles sized, followed by the mannitol, whereas the erythritol applied (a non-DC grade of erythritol) had significantly larger particles. Using the non-DC grade erythritol with larger particles resulted in relatively fast dissolution times.

Example 34

Evaluations of Two-Layered Tablets—Whole Tablet of Tablet No. 45

Tablet no. 45 were made with the compression forces indicated in Table 30.

TABLE 30

Whole two-layered tablets.

| Compression force Layer 1 | Compression force Layer 2 | Fragility | Dissolution time |
| --- | --- | --- | --- |
| 10 kN | 5 kN | Fragile. Decapping layer 1 from layer 2 | N/A |
| 5 kN | 5 kN | Not fragile. No decapping | layer 1: 5 min 20 sec layer 2: 1 min |
| 8 kN | 5 kN | Not fragile. No decapping | layer 1: 6 min layer 2: 1 min |
| 5 kN | 2 kN | Not fragile. No decapping | Layer 1: 5 min 30 sec Layer 2: 45 sec. |

Table 30 shows that it is possible to compress layer 1 with a compression force that is higher than the compression force applied to layer 2, while still obtaining tablets that are not too fragile. It is noted, however, that decapping of layer 2 from layer 1 may be avoided if the compression force applied to layer 1 is not too high.

Furthermore, the measured dissolution times were fully acceptable, particularly since the second layers dissolved within 1 minute, whereas the first layers all took more than 5 minutes to dissolve.

Example 35

In Vivo Testing of Release

A sample tablet was tested in a test panel of 8 test persons. Test subjects abstain from eating and drinking at least 30 minutes before initiation of any test. The test person was a healthy person appointed on an objective basis according to specified requirements. After 0, 0.5, 1, 2, 3, 5 and 10 minutes, the content of CBD was measured in the remaining tablet residue. The tablet was subject to triple measurements for each of the 8 test persons, giving a total of 24 measurements for each sample. An average of the 24 measurements was calculated and the weight % release was calculated based on the original content of CBD in the sample. The content of CBD was measured in the remaining tablet residue, if still present.

The tablet was weighted and placed in the mouth, between the tongue and the palate. The tablet was sucked and turned every 0.5 minute. Once the desired test time was achieved (0.5, 1, 2, 3, 5 and 10 min.), the tablet was taken out and weighed directly into a measuring glass to be used for analysis of API content. An in vivo dissolution profile was obtained by analyzing the content of the API in the tablet at different dissolution times.

Example 36

In Vitro Testing of Release

A sample tablet was tested. After 0, 0.5, 1, 2, 3, 5 and 10 minutes, the content of CBD was measured in the remaining tablet residue. The tablet was subject to triple measurements. An average of the measurements was calculated and the weight % release was calculated based on the original content of CBD in the sample. The content of CBD was measured in the remaining tablet residue, if still present.

The tablet was weighted. Then 25 ml of phosphate buffer was added into a 50 ml measuring tube with screw cap. The tablet was added to the tube. The tube was fixed horizontally on a shaking table. After shaking, the tablet was analyzed for content of API. An in vitro profile was obtained by analyzing the content of the API in the tablet at different dissolution times.

Example 37

CBD Delivered to the Oral Mucosa

A sample was sucked for 1 minute in a test panel of 8 test persons. Test subject abstains from eating and drinking at least 30 minutes before initiation of any test. The test person was not allowed to swallow during the procedure. The tablet was weighted and placed in the mouth, between the tongue and the palate. The tablet was sucked and turned every 10 seconds. After one minute, saliva was obtained from the test person and collected in a vessel for later analysis. In tests for 2 minutes release, the same procedure was followed until 2 minutes where the last saliva sample was collected and added to the same vessel for aggregated analysis. The test person was a healthy person appointed on an objective basis according to specified requirements. The aggregated saliva sample was collected after 2 minutes, and the content of CBD was measured in the saliva. The content of CBD was also measured in the remaining residue. The residue, if still present, was positioned in a flask, weighted and analyzed. The residue, if still present, and saliva were subject to 3 triple measurements for each of the 8 test persons, giving a total of 24 measurement for each sample. An average of the 24 measurements was calculated and the weight % release was calculated. By comparing the amount of CBD in the residue and the amount of CBD in the saliva, the amount of CBD delivered to the oral mucosa could be estimated.

Example 38

Sensoric Evaluation Test Set-Up

In addition to release measurements, either in vivo or in vitro, sensoric tests were performed to reveal very important characteristics and properties of the tablets. These sensoric parameters are important as indicators of the structure of the tablet composition. The structure is the underlying guidance as to how the tablet resembles the structure of a comparative tablet, which is set as the standard in the test series, i.e. the tablets are compared to each other in the test series of preferably 5 samples. The test set-up was composed of 8 test persons in a test panel. All of the test persons were healthy individuals appointed on an objective basis according to specified requirements. The sensory analysis was performed according to ISO 4121-2003 in testing conditions following ISO 8589. The result is an average of the results of the 8 individuals.

The test persons gave a rating from "+" to "+++++", where "+" is poor and "+++++" is excellent, i.e. "+++++" means that the tablet was excellent compared to the standard, "+++" means that the tablet was comparable to the standard and "+" means that the tablet was very far from comparable to the standard. "0" indicated that it was not tested.

Four different parameters were tested in a test panel:

| Friability | Flavor | Sweetness | Off-notes |
| --- | --- | --- | --- |

"Friability"—the impression of the tablet when placed in the mouth and sucking is commenced. For instance, a very hard and viscous structure gave a very low rating and a very brittle structure also gave a very low rating.

"Flavor"—the overall impression of the tablet during sucking with respect to flavor. For instance, a very low flavor experience gave a very low rating and a too high flavor experience that was not comparable to the standard also gave a very low rating.

"Sweetness"—the overall impression of the taste of the tablet during sucking with respect to sweetness. For instance, if the sweetness was decreasing rapidly, a very low rating was given and if the sweetness was too high giving an uncomfortable feeling, a very low rating was also given.

"Off-notes"—the overall impression of the off-note from the one or more cannabinoids in the composition during sucking. For instance, if off-notes (grass, bitter notes, irritation in the throat) were experienced in the throat, a low rating was given and if other uncomfortable sensations was experienced, a low rating was also given.

The invention claimed is:

1. A cannabinoid tablet, the tablet comprising at least two tablet modules including:
   a fast-disintegrating tablet module comprising:
      a sugar alcohol composition comprising one or more sugar alcohol particles in an amount of 20 to 90% by weight of the fast-disintegrating tablet module,
      a cannabinoid composition comprising one or more cannabinoids, and
      a disintegrant composition comprising one or more disintegrants operable to disintegrate the fast-disintegrating module in 2 minutes or less than 2 minutes in contact with oral saliva, and
   a lozenge tablet module that is different in composition than the fast-disintegrating tablet module, the lozenge tablet module comprising:
      a sugar alcohol composition comprising one or more sugar alcohol particles, and
      a flavor composition comprising one or more flavor components,
   wherein the lozenge tablet module disintegrates in about 3 minutes or more than 3 minutes in contact with oral saliva and does not comprise a disintegrant.

2. The tablet according to claim 1, wherein the one or more disintegrants is present in an amount of 0.5 to 25% by weight of the tablet.

3. The tablet according to claim 1, wherein the one or more disintegrants is swellable in contact with oral saliva.

4. The tablet according to claim 1, wherein the one or more disintegrants comprises starch.

5. The tablet according to claim 1, wherein the one or more disintegrants comprises microcrystalline cellulose.

6. The tablet according to claim 1, wherein the one or more disintegrants comprises a super disintegrant.

7. The tablet according to claim 1, wherein the one or more disintegrants comprises a super disintegrant of a cross-linked polymer.

8. The tablet according to claim 1, wherein the one or more disintegrants comprises a super disintegrant selected from the group consisting of sodium croscarmellose, crospovidone, sodium starch glycolate and combinations thereof.

9. The tablet according to claim 1, wherein the one or more disintegrants comprises cross-linked polyvinylpyrrolidone.

10. The tablet according to claim 1, wherein at least a part of the one or more cannabinoids is reversibly associated with at least a part of the one or more sugar alcohol particles.

11. The tablet according to claim 1, wherein the weight ratio of the one or more cannabinoids relative to the one or more sugar alcohol particles is from 1:30 to 1:1.

12. The tablet according to claim 1, further comprising at least one dissolution modifier selected from the group consisting of alginic acid or a salt thereof, polycarbophil or a salt thereof, xanthan gum and mixtures thereof.

13. The tablet according to claim 1, wherein the one or more cannabinoids comprises cannabidiol (CBD).

14. The tablet according to claim 1, wherein the tablet comprises a self-emulsifying agent.

15. The tablet according to claim 1, wherein the tablet comprises a lipid carrier for the one or more cannabinoids.

16. The tablet according to claim 1, wherein the lozenge tablet module comprises one or more cannabinoids.

17. The tablet according to claim 1, wherein the one or more sugar alcohol particles of the lozenge tablet module have an average particle size that is larger than an average particle size of the one or more sugar alcohol particles of the fast-disintegrating tablet module.

18. The tablet according to claim 1, wherein the lozenge tablet module 50-90% by weight of the total tablet.

19. The tablet according to claim 1, wherein the lozenge tablet module is tableted in a separate step with a higher pressure before tableting the fast-disintegrating tablet module.

20. A cannabinoid tablet, the tablet comprising at least two tablet modules including:
a fast-disintegrating tablet module comprising:
a sugar alcohol composition comprising one or more sugar alcohol particles in an amount of 20% to 90% by weight of the fast-disintegrating tablet module,
a cannabinoid composition comprising one or more cannabinoids, and
a disintegrant composition comprising one or more disintegrants operable to disintegrate the fast-disintegrating tablet module in 2 minutes or less than 2 minutes in contact with oral saliva, and
a lozenge tablet module that is different in composition than the fast-disintegrating tablet module comprising:
a sugar alcohol composition comprising one or more sugar alcohol particles,
a cannabinoid composition comprising one or more cannabinoids,
wherein the lozenge tablet module disintegrates in about 3 minutes or more than 3 minutes in contact with oral saliva and does not comprise a disintegrant.

21. A cannabinoid tablet, the tablet comprising at least two tablet modules including:
a fast-disintegrating tablet module comprising:
a sugar alcohol composition comprising one or more sugar alcohol particles in an amount of 20% to 90% by weight of the fast-disintegrating tablet module,
a cannabinoid composition comprising one or more cannabinoids, and
a disintegrant composition comprising one or more disintegrants operable to disintegrate the fast-disintegrating tablet module in 2 minutes or less than 2 minutes in contact with oral saliva, and
a lozenge tablet module that is different in composition than the fast-disintegrating tablet module comprising:
a sugar alcohol composition comprising one or more sugar alcohol particles, and
a flavor composition comprising one or more flavor components,
wherein the lozenge tablet module disintegrates in about 3 minutes or more than 3 minutes in contact with oral saliva and constitutes 50-90% by weight of the total tablet.

* * * * *